(12) United States Patent
Imai et al.

(10) Patent No.: US 11,583,487 B2
(45) Date of Patent: Feb. 21, 2023

(54) METHOD FOR PRODUCING COATING

(71) Applicant: KAO CORPORATION, Tokyo (JP)

(72) Inventors: Asuka Imai, Cincinnati, OH (US);
Nobuyuki Asami, Tokyo (JP)

(73) Assignee: KAO CORPORATION, Tokyo (JP)

( * ) Notice: Subject to any disclaimer, the term of this patent is extended or adjusted under 35 U.S.C. 154(b) by 446 days.

(21) Appl. No.: 16/527,844

(22) Filed: Jul. 31, 2019

(65) Prior Publication Data

US 2020/0046618 A1    Feb. 13, 2020

Related U.S. Application Data (60) Provisional application No. 62/716,485, filed on Aug. 9, 2018.

(51) Int. Cl.

| | | |
|---|---|---|
| *A61K 9/00* | (2006.01) | |
| *A61K 8/35* | (2006.01) | |
| *A61Q 1/02* | (2006.01) | |
| *A61K 8/92* | (2006.01) | |
| *A45D 34/00* | (2006.01) | |
| *A61K 8/34* | (2006.01) | |
| *A61K 8/81* | (2006.01) | |
| *A61K 8/06* | (2006.01) | |

(52) U.S. Cl.
CPC ............... *A61K 8/35* (2013.01); *A45D 34/00* (2013.01); *A61K 8/062* (2013.01); *A61K 8/345* (2013.01); *A61K 8/8117* (2013.01); *A61K 8/8152* (2013.01); *A61K 8/92* (2013.01); *A61Q 1/02* (2013.01); *A45D 2034/005* (2013.01); *A61K 2800/87* (2013.01)

(58) Field of Classification Search
CPC ... A61K 8/02; A61K 8/34; A61K 8/81; A61K 8/73; A61K 9/0002; A61K 9/0012; A61K 9/014; A61K 9/0087
See application file for complete search history.

(56) References Cited

U.S. PATENT DOCUMENTS

| | | | |
|---|---|---|---|
| 6,311,903 B1 | 11/2001 | Gaw et al. | |
| 6,318,647 B1 | 11/2001 | Gaw et al. | |
| 6,531,142 B1 | 3/2003 | Rabe et al. | |
| 8,048,920 B2 | 11/2011 | Jeorger et al. | |
| 2001/0020652 A1 | 9/2001 | Kadlubowski et al. | |
| 2001/0020653 A1 | 9/2001 | Wilson et al. | |
| 2001/0023902 A1 | 9/2001 | Wilson et al. | |
| 2001/0038047 A1 | 11/2001 | Wilson et al. | |
| 2005/0002976 A1 | 1/2005 | Wu | |
| 2009/0148393 A1 | 6/2009 | Maitra | |
| 2011/0076244 A1 | 3/2011 | Hammer | |
| 2013/0034513 A1 | 2/2013 | Samain | |
| 2016/0219874 A1* | 8/2016 | Yarin | ........................ D01F 1/10 |
| 2019/0053602 A1 | 2/2019 | Amari et al. | |

FOREIGN PATENT DOCUMENTS

| | | | | |
|---|---|---|---|---|
| AU | 2016-340485 A1 | 5/2018 | | |
| CN | 108135789 A | 6/2018 | | |
| FR | 2 910 285 B1 | 4/2014 | | |
| JP | 2003-507165 A | 2/2003 | | |
| JP | 2006-104211 A | 4/2006 | | |
| JP | 2017-78062 A | 4/2017 | | |
| JP | 2017078062 A * | 4/2017 | ............ | A45D 34/04 |
| TW | 201729785 A | 9/2017 | | |
| WO | WO-2017069079 A1 * | 4/2017 | ............ | A45D 34/04 |
| WO | WO 2018/124227 A1 | 7/2018 | | |

OTHER PUBLICATIONS

PDMS for polydimethylsiloxane: https://www.mit.edu/~6.777/matprops/pdms.htm (Year: 2004).*
International Search Report and Written Opinion dated Nov. 1, 2019 in PCT/US19/44927, 14 pages.

* cited by examiner

*Primary Examiner* — Micah Paul Young
(74) *Attorney, Agent, or Firm* — Oblon, McClelland, Maier & Neustadt, L.L.P.

(57) ABSTRACT

A method for producing a coating on skin, the method comprising: A) a step of electrostatically spraying a composition X comprising the following component (a) and the following component (b) directly on the skin to thereby form a coating on a skin surface: (a) one or more volatile substances selected from the group consisting of water, an alcohol, and a ketone, and (b) a polymer having a coating forming ability; and B) a step of applying a composition Y, other than the composition X, containing the following component (c) and the following component (d) to the skin: (c) 5% by mass or more and 20% by mass or less of an adhesive polymer, and (d) 1% by mass or more and 40% by mass or less of a polyol, in this order or in reverse order.

20 Claims, 1 Drawing Sheet

METHOD FOR PRODUCING COATING

TECHNICAL FIELD

The present invention relates to a method for producing a coating.

BACKGROUND ART

Methods for forming a coating on skin by electrostatic spraying have been reported. For example, Patent Literature 1 describes a method of treating skin by electrostatically spraying a composition on the skin. The composition to be used in this method contains a liquid insulating substance, an electroconductive substance, a granular powdery substance and a thickener. As with such a composition, typically a cosmetic or a skin care composition containing pigments is used. Specifically, a cosmetic foundation is used as the composition. That is, the invention described in Patent Literature 1 mainly contemplates making up skin by electrostatically spraying a cosmetic foundation for the purpose of beauty. Patent Literature 2 describes a disposable cartridge to be used in an electrostatic spray apparatus for cosmetics.

When coatings are formed on skin by electrostatic spraying according to the methods described in Patent Literatures 1 and 2, however, it has been found that the adhesiveness between the skin and the coatings formed by electrostatic spraying is not sufficient and the coatings break or peel due to external forces such as friction. Now, the present applicant has found that when a liquid agent comprising water, a polyol or an oil liquid at 20° C. is applied before or after a coating is formed on skin by electrostatic spraying, the adhesiveness of the coating obtained by the electrostatic spraying is improved (Patent Literature 3).
[Patent Literature 1] JP-A-2006-104211
[Patent Literature 2] JP-A-2003-507165
[Patent Literature 3] JP-A-2017-78062

SUMMARY OF INVENTION

The present invention provides a method for producing a coating on skin, the method comprising:
A) a step of electrostatically spraying a composition X comprising the following component (a) and the following component (b) directly on the skin to thereby form a coating on a skin surface:
(a) one or more volatile substances selected from the group consisting of water, an alcohol, and a ketone, and
(b) a polymer having a coating forming ability; and
B) a step of applying a composition Y, other than the composition X, comprising the following component (c) and the following component (d) to the skin:
(c) 5% by mass or more and 20% by mass or less of an adhesive polymer, and
(d) 1% by mass or more and 40% by mass or less of a polyol,
in this order or in reverse order.

The present invention further provides a composition Y for applying to a skin surface, wherein the composition Y is a composition used for producing a coating on the skin by applying the composition to the skin by using a unit other than electrostatic spraying to thereby produce a coating on the skin, before or after a coating is formed on a skin surface by electrostatically spraying a composition directly on the skin, and comprises the following component (c) and the component (d):

(c) 5% by mass or more and 20% by mass or less of an adhesive polymer, and
(d) 1% by mass or more and 40% by mass or less of a polyol.

The present invention further provides a method for applying a composition Y to the skin, the method being a method used for producing a coating on the skin by applying the composition Y to the skin by using a unit other than electrostatic spraying, before or after a coating is formed on a skin surface by electrostatically spraying a composition directly on the skin, wherein the composition Y comprises the following component (c) and the following component (d):

(c) 5% by mass or more and 20% by mass or less of an adhesive polymer, and
(d) 1% by mass or more and 40% by mass or less of a polyol.

DETAILED DESCRIPTION OF INVENTION

It has become clear, however, that the coatings obtained by the conventional methods, though being excellent in adhesiveness with skin, when applied to skin portions where movements are present, cannot follow the movements and this causes peeling off of the coating to the skin due to contact with clothes in some cases.

The present inventors have studied the compositions to be applied before or after electrostatic spraying on skin, and have found that use of a composition comprising an adhesive polymer and a polyol different from a composition used for the electrostatic spraying enables formation of coating excellent in scratch resistance and extensibility.

The coating obtained by the present invention has excellent scratch resistance and is not easily peeled off due to contact with clothes and the like. The coating further has excellent extensibility, and even when being formed on portions where movements of skin are present, never peels off.

The method of the present invention comprises A) the step (step A) of electrostatically spraying a composition X directly on skin to thereby form a coating on a skin surface, and the step (step B) of applying a composition Y on the skin.

As a method for forming the coating in the step A, the present invention adopts an electrostatic spray method. The electrostatic spray method is a method in which a positive or negative high voltage is applied to a composition to charge the composition, and the charged composition is sprayed toward a target. The sprayed composition, while repeating micronization by the Coulomb repulsive force, spreads in a space, and in the course, or after the sprayed composition is adhered on the target, a solvent serving as a volatile substance dries to thereby form the coating on a surface of the target.

The above-mentioned composition X (hereinafter, referred to also as "spraying composition") to be used in the present invention is a liquid in an environment where the electrostatic spray method is carried out. The composition X comprises the following component (a) and component (b).

Component (a) One or more volatile substances selected from the group consisting of water, an alcohol, and a ketone.
Component (b) A polymer having a coating forming ability.

Hereinafter, the each component will be described.

The volatile substance of the component (a) is a substance having volatility in its liquid state. The component (a) is blended in the spraying composition for the purpose that the spraying composition placed in an electric field, after being fully charged, is discharged toward skin from a nozzle tip, and the charge density of the spraying composition becomes excessive as the component (a) evaporates, and the component (a) further evaporates while the component (a) is further micronized by the Coulomb repulsion to thereby finally form a dry coating on the skin. For this purpose, the vapor pressure at 20° C. of the volatile substance is preferably 0.01 kPa or more and 106.66 kPa or less, more preferably 0.13 kPa or more and 66.66 kPa or less, even more preferably 0.67 kPa or more and 40.00 kPa or less and further more preferably 1.33 kPa or more and 40.00 kPa or less.

Among the volatile substances of the component (a), an alcohol can be used, for example, a monohydric chain aliphatic alcohol, a monohydric alicyclic alcohol or a monohydric aromatic alcohol. The monohydric aliphatic alcohol includes $C_1$ to $C_6$ alcohols; the monohydric alicyclic alcohol includes $C_4$ to $C_6$ cyclic alcohols; and the monohydric aromatic alcohol includes benzyl alcohol and phenylethyl alcohol. Specific examples thereof include ethanol, isopropyl alcohol, butyl alcohol, phenylethyl alcohol, n-propanol and n-pentanol. For the alcohol, one or more selected from these alcohols can be used.

Among the volatile substances of the component (a), the ketone includes di-$C_1$-$C_4$ alkyl ketones such as acetone, methyl ethyl ketone and methyl isobutyl ketone. These ketones can be used singly or in a combination of two or more.

The volatile substance of the component (a) is preferably one or more selected from the group consisting of ethanol, isopropyl alcohol, butyl alcohol and water, more preferably one or more selected from the group consisting of ethanol and butyl alcohol, and even more preferably a volatile substance containing at least ethanol.

The content of the component (a) in the spraying composition is preferably 30% by mass or more, more preferably 55° by mass or more and even more preferably 60° by mass or more. Then the content is preferably 98% by mass or less, more preferably 96% by mass or less and even more preferably 94% by mass or less. The content of the component (a) in the spraying composition is preferably 30% by mass or more and 98% by mass or less, more preferably 55% by mass or more and 96% by mass or less and even more preferably 60% by mass or more and 94% by mass or less. Incorporation of the component (a) in this proportion in the spraying composition enables the spraying composition to be sufficiently volatilized when the electrostatic spray method is carried out.

Ethanol is, with respect to the total amount of the volatile substances of the component (a), preferably 50% by mass or more, more preferably 65% by mass or more and even more preferably 80% by mass or more. Further, being 100% by mass or less is preferable. Ethanol is, with respect to the total amount of the volatile substances of the component (a), preferably 50% by mass or more and 100% by mass or less, more preferably 65% by mass or more and 100% by mass or less and even more preferably 80° by mass or more and 100° by mass or less.

The polymer having the coating forming ability as the component (b) is usually a substance which can be dissolved in the volatile substance as the component (a). Here, being dissolved refers to being in a dispersed state at 20° C., which dispersed state is a visually homogeneous state, preferably a visually transparent or translucent state.

As the polymer having the coating forming ability, a suitable one is used according to the property of the volatile substance of the component (a). Specifically, the polymers having the coating forming ability are roughly classified into water-soluble polymers and water-insoluble polymers. In the present description, the "water-soluble polymer" refers to a polymer having such a property that 1 g of the polymer is weighed in the environment of 1 atm and 23° C., and thereafter dipped in 10 g of ion-exchange water, and after an elapse of 24 hours, 0.5 g or more of the dipped polymer dissolves in the water. On the other hand, in the present description, the "water-insoluble polymer" refers to a polymer having such a property that 1 g of the polymer is weighed in the environment of 1 atm and 23° C., and thereafter dipped in 10 g of ion-exchange water, and after an elapse of 24 hours, 0.5 g or more of the dipped polymer does not dissolve in the water.

Examples of the water-soluble polymer having the coating forming ability include mucopolysaccharides such as pullulan, hyaluronic acid, chondroitin sulfuric acid, poly-γ-glutamic acid, denatured cornstarch, β-glucan, glucooligosaccharides, heparin and keratosulfuric acid, natural polymers such as cellulose, pectin, xylan, lignin, glucomannan, galacturonic acid, psyllium seed gum, tamarind seed gum, gum arabic, tragacanth gum, soybean water-soluble polysaccharides, alginic acid, carrageenan, laminaran, agar (agarose), fucoidan, methylcellulose, hydroxypropylcellulose and hydroxypropylmethylcellulose, and synthetic polymers such as partially saponified polyvinyl alcohols (if not used concurrently with a crosslinking agent), low-saponified polyvinyl alcohols, polyvinyl pyrrolidone (PVP), polyethylene oxide and sodium polyacrylate. These water-soluble polymers can be used singly or in a combination of two or more. Among these water-soluble polymers, from the viewpoint of ease of production of coatings, it is preferable to use pullulan, and synthetic polymers such as partially saponified polyvinyl alcohols, low-saponified polyvinyl alcohols, polyvinyl pyrrolidone and polyethylene oxide. In the case of using a polyethylene oxide as the water-soluble polymer, the number-average molecular weight thereof is preferably 50,000 or more and 3,000,000 or less and more preferably 100,000 or more and 2,500,000 or less.

On the other hand, examples of the water-insoluble polymer having the coating forming ability include completely saponified polyvinyl alcohols which can be insolubilized after formation of coatings, partially saponified polyvinyl alcohols which can be crosslinked after formation of coatings by using a crosslinking agent concurrently, oxazoline-modified silicones of poly(N-propanoylethyleneimine)-graft-dimethylsiloxane/γ-aminopropylmethylsiloxane copolymers or the like, polyvinylacetal diethylaminoacetate, zein (major component of corn protein), polyester, polylactic acid (PLA), acryl resins such as polyacrylonitrile resins and polymethacrylate resins, polystyrene resins, polyvinylbutyral resins, polyethylene terephthalate resins, polybutylene terephthalate resins, polyurethane resins, polyamide resins, polyimide resins and polyamideimide resins. These water-insoluble polymers can be used singly or in a combination of two or more. Among these water-insoluble polymers, it is preferable to use one or more selected from the group consisting of completely saponified polyvinyl alcohols which can be insolubilized after formation of coatings, partially saponified polyvinyl alcohols which can be crosslinked after formation of coatings by using a crosslinking agent concurrently, polyvinylbutyral resins, polyurethane resins, oxazoline-modified silicones of poly(N-propanoylethyleneimine)-graft-dimethylsiloxane/γ-aminopropylmethylsiloxane copolymers or the like, polyvinylacetal diethylaminoacetate and zein; and it is more preferable to use one or more selected from the group consisting of polybutyral resins and polyurethane resins.

The content of the component (b) in the spraying composition is preferably 2% by mass or more, more preferably 4% by mass or more and even more preferably 6% by mass or more. The content is preferably 50% by mass or less, more preferably 45% by mass or less and even more preferably 40% by mass or less. The content of the component (b) in the spraying composition is preferably 2% by mass or more and 50% by mass or less, more preferably 4% by mass or more and 45% by mass or less and even more preferably 6% by mass or more and 40% by mass or less. By blending the component (b) in this proportion in the spraying composition, there can be successfully formed a coating being composed of a deposit of fibers, masking the surface of bare skin, being excellent in scratch resistance and extensibility, and being excellent in cosmetic persistency.

The ratio of the contents of the component (a) and the component (b), ((a)/(b)), in the spraying composition is, from the viewpoint that the component (a) can be sufficiently volatilized when the electrostatic spray method is carried out, preferably 0.5 or more and 40 or less, more preferably 1 or more and 30 or less and even more preferably 1.3 or more and 25 or less.

The ratio of ethanol and the content of the component (b), (ethanol/(b)), in the spraying composition is, from the viewpoint that ethanol can be sufficiently volatilized when the electrostatic spray method is carried out, preferably 0.5 or more and 40 or less, more preferably 1 or more and 30 or less and even more preferably 1.3 or more and 25 or less.

The spraying composition can further comprise a glycol. The glycol incudes ethylene glycol, propylene glycol, butylene glycol, diethylene glycol, dipropylene glycol and polypropylene glycol. From the viewpoint of ability to sufficiently volatilize the component (a) when the electrostatic spray method is carried out, the glycol is, in the spraying composition, preferably 10% by mass or less and more preferably 8% by mass or less.

Further, water is, from the viewpoint of fiber formability and electroconduction, with respect to the total amount of the volatile substances of the component (a), preferably less than 50% by mass, more preferably 45% by mass or less, even more preferably 10% by mass or less and further more preferably 5% by mass or less, and preferably 0.2% by mass or more and more preferably 0.4% by mass or more.

The spraying composition can further comprise a powder. The powder includes coloring pigments, extender pigments, pearl pigments and organic powders. The powder is, from the viewpoint of imparting smooth feel to skin surfaces, in the spraying composition, preferably 5% by mass or less, more preferably 3% by mass or less and even more preferably 1% by mass or less, and it is preferable to contain substantially no powder.

The spraying composition may comprise only the above-mentioned component (a) and component (b), or may contain, in addition to the component (a) and component (b), other components. Examples of the other components include oils such as di(phytosteryl/octyldodecyl) lauroylglutamate, surfactants, UV protective agents, fragrances, repellants, antioxidants, stabilizers, antiseptics, antiperspirants and various vitamins. Here, these agents are not limited to their original applications as the agents, but can be used for other applications according to purposes, for example, an antiperspirant can be used as a fragrance. Alternatively, these agents can be used as having multiple purposes; for example, an antiperspirant can also serve as a fragrance. In the case where the spraying composition contains the other components, the content rate of the other components is preferably 0.1% by mass or more and 30% by mass or less and more preferably 0.5% by mass or more and 20% by mass or less.

In the method of the present invention, before or after the step B, a coating is formed directly on a skin surface by electrostatically spraying the spraying composition. That is, in the method of the present invention, the order of the step A and the step B may be, step A→step B, or step B→step A.

In the case of carrying out the electrostatic spray method, there is used a spraying composition whose viscosity at 25° C. is preferably 1 mPa·s or more, more preferably 10 mPa·s or more and even more preferably 50 mPa·s or more. There is used the spraying composition whose viscosity at 25° C. is preferably 5,000 mPa-s or less, more preferably 2,000 mPa·s or less and even more preferably 1,500 mPa·s or less. The viscosity at 25° C. of the spraying composition is preferably 1 mPa·s or more and 5,000 mPa-s or less, more preferably 10 mPa·s or more and 2,000 mPa·s or less and even more preferably 50 mPa·s or more and 1,500 mPa·s or less. By using the spraying composition having a viscosity in this range, there can be successfully formed a coating, particularly a porous coating composed of a deposit of fibers, by the electrostatic spray method. The formation of the porous coating is advantageous from the viewpoint of improving prevention of stuffiness of skin, from the viewpoint of improving adhesiveness of the coating to skin, from the viewpoint that the coating, when peeled off the skin, can be peeled off easily and cleanly, and from other viewpoints. The viscosity of the spraying composition is measured at 25° C. by using an E-type viscometer. As the E-type viscometer, for example, an E-type viscometer, manufactured by Tokyo Keiki Inc. can be used. As a rotor in this case, a rotor No. 43 can be used.

Figure 1:
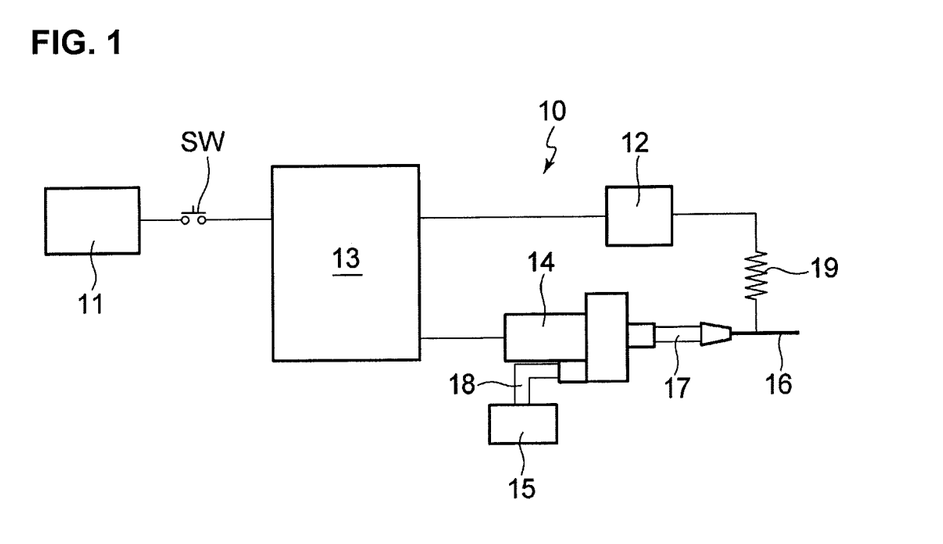
FIG. 1 is a schematic diagram showing an electrostatic spray apparatus suitably used in the present invention.

The spraying composition is sprayed directly on a skin of a human by the electrostatic spray method. The electrostatic spray method comprises, in an electrostatic spraying step, a step of electrostatically spraying the spraying composition on a skin by using an electrostatic spray apparatus to thereby form a coating. The electrostatic spray apparatus has a container accommodating the spraying composition, a nozzle for discharging the spraying composition, a supply device for supplying the spraying composition accommodated in the container to the nozzle, and a power source for applying a voltage to the nozzle. FIG. 1 shows a schematic diagram indicating a schematic of an electrostatic spray apparatus suitably used in the present invention. An electrostatic spray apparatus 10 shown in FIG. 1 has a low-voltage power source 11. The low-voltage power source 11 is one which can generate a voltage of several volts to several tens of volts. For the purpose of enhancing transportability of the electrostatic spray apparatus 10, it is preferable that the low-voltage power source 11 be composed of one or more batteries. Use of batteries as the low-voltage power source 11 exhibits also such an advantage that the batteries can be exchanged easily as required. In place of the batteries, an AC adaptor or the like can be used as the low-voltage power source 11.

The electrostatic spray apparatus 10 has also a high-voltage power source 12. The high-voltage power source 12 is connected to the low-voltage power source 11, and has an electronic circuit (not shown in figure) for boosting a voltage generated by the low-voltage power source 11 to a high voltage. The boosting electronic circuit is usually constituted of a transformer, capacitors, semiconductor elements and the like.

The electrostatic spray apparatus 10 further has an auxiliary electric circuit 13. The auxiliary electric circuit 13 intervenes between the above-mentioned low-voltage power source 11 and high-voltage power source 12, and has a function of regulating the voltage of the low-voltage power source 11 to cause the high-voltage power source 12 to stably operate. The auxiliary electric circuit 13 further has a function of controlling the rotation frequency of a motor equipped with a pump mechanism 14 described later. The control of the rotation frequency of the motor leads to control of the amount of the spraying composition supplied from a container 15 described later of the spraying composition to the pump mechanism 14. A switch SW is installed between the auxiliary electric circuit 13 and the low-voltage power source 11, and is so configured that the electrostatic spray apparatus 10 can be operated/stopped by on/off of the switch SW.

The electrostatic spray apparatus 10 further has a nozzle 16. The nozzle 16 is composed of various electroconductors including metals and non-electroconductors such as plastics, rubbers and ceramics, and has a shape which can discharge the spraying composition from its tip. In the nozzle 16, a fine space through which the spraying composition flows is formed along the longitudinal direction of the nozzle 16. It is preferable that the size of the fine space be 100 μm or more and 1,000 μm or less in diameter. The nozzle 16 communicates with the pump mechanism 14 through a pipe 17. The pipe 17 may be an electroconductor or a non-electroconductor. The nozzle 16 is electrically connected to the high-voltage power source 12. Thereby, the nozzle 16 is so configured that a high voltage can be applied thereto. In this case, in order to prevent an excessive current from flowing in a human body when the human body touches directly the nozzle 16, the nozzle 16 and the high-voltage power source 12 are electrically connected through a current limiting resistance 19.

The pump mechanism 14 communicating with the nozzle 16 through the pipe 17 functions as a supply device for supplying the spraying composition accommodated in the container 15 to the nozzle 16. The pump mechanism 14 operates by receiving a power from the low-voltage power source 11. The pump mechanism 14 is constituted so as to supply a predetermined amount of the spraying composition to the nozzle 16 under control by the auxiliary electric circuit 13.

To the pump mechanism 14, the container 15 is connected through a flexible pipe 18. The spraying composition is accommodated in the container 15. It is preferable that the container 15 have a cartridge-type exchangeable form. It is preferable that the pump mechanism 14 be of a gear pump type or a piston pump type.

Figure 2:
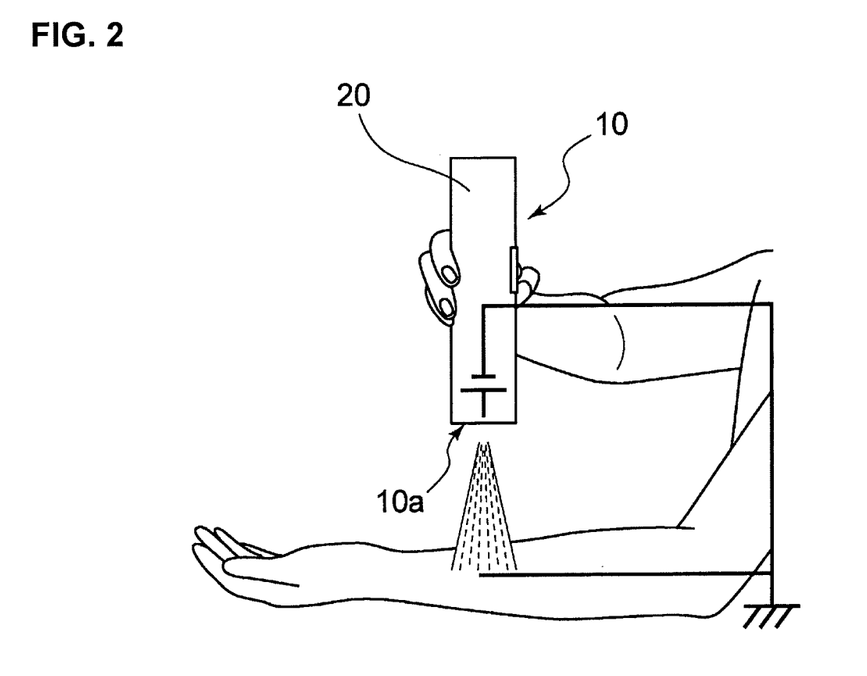
FIG. 2 is an illustrative view showing the state of carrying out an electrostatic spray method using an electrostatic spray apparatus.

The electrostatic spray apparatus 10 having the above constitution can be used, for example, as shown in FIG. 2. FIG. 2 shows a hand-held type electrostatic spray apparatus 10 having a size holdable by one hand. The electrostatic spray apparatus 10 shown in the figure is so configured that all members of the constitutional diagram shown in FIG. 1 are accommodated in a cylindrical housing 20. On one end 10a in the longitudinal direction of the housing 20, a nozzle (not shown in figure) is disposed. The nozzle is arranged on the housing 20 so as to protrude toward a skin side as a coating forming target so that the jetting direction of the composition is made to coincide with the longitudinal direction of the housing 20. By arranging the nozzle so that the nozzle tip protrudes toward a coating forming target in the longitudinal direction of the housing 20, it becomes hard for the spraying composition to adhere on the housing and a coating can be formed stably.

In the case where a skin as the coating forming target is a user's own skin, when an electrostatic spray apparatus 10 is operated, the user, that is, a person forming a coating on the person's own skin by electrostatic spraying, holds the apparatus 10 by hand and directs one end 10a of the apparatus 10 having a nozzle (not shown in figure) arranged thereon toward a target site of electrostatic spraying. FIG. 2 illustrates a state that the one end 10a of the electrostatic spray apparatus 10 is directed to an inner side of the user's forearm. Under this state, a switch of the apparatus 10 is turned on to carry out the electrostatic spray method. A power is supplied to the apparatus 10 to generate an electric field between the nozzle and the skin. In an embodiment illustrated in FIG. 2, a high positive voltage is applied to the nozzle and the skin becomes a negative electrode. When the electric field is generated between the nozzle and the skin, the spraying composition on the nozzle tip is depolarized by electrostatic induction and the frontend portion of the spraying composition spreads to a cone-like shape; and charged droplets of the spraying composition are discharged from the spread cone frontend along the electric field into the air toward the skin. As the component (a) serving as a solvent evaporates from the charged spraying composition discharged into the space and, the charge density of the surface of the spraying composition becomes excessive, so that while micronization of the spraying composition is repeated by the Coulomb repellency, the spraying composition spreads into the space and reaches the skin. In this case, by suitably regulating the viscosity of the spraying composition, the sprayed spraying composition can be made to reach the skin in the state of being droplets. Alternatively, it is also possible that while during the discharge into the space, the component (a) of a volatile substance serving as a solvent is caused to volatilize from the composition to cause a polymer serving as a solute having the coating forming ability to solidify, the spraying composition is caused to extensionally deform due to a potential difference and form fibers, which deposit on the surface of the skin. For example, when the viscosity of the spraying composition is raised, it becomes easy for the composition to be deposited in a form of fibers on the skin surface. Thereby, a coating composed of a deposit of the fibers is formed on the skin surface. A coating composed of a deposit of fibers is possible to form also by regulating the distance between the nozzle and the skin, and the voltage applied to the nozzle.

During carrying out of the electrostatic spray method, a high potential difference is generated between the skin serving as a coating forming target and the nozzle. Since the impedance is very high, however, the current flowing in the human body is remarkably minute. The present inventors have confirmed that the current flowing in a human body during carrying out of the electrostatic spray method is lower by several digits than, for example, the current flowing in human bodies due to a static electricity generated in usual lives.

In forming a deposit of fibers by the electrostatic spray method, the thickness of the fibers is, in terms of equivalent circle diameter, preferably 10 nm or more and more preferably 50 nm or more. The thickness is preferably 3,000 nm or less and more preferably 2,000 nm or less. The thickness of the fibers can be measured, for example, by observing the fibers in a magnification of 10,000× by a scanning electron microscope (SEM) observation, arbitrarily choosing 10 fibers excluding defects (lumps of fibers, crossing portions of fibers, droplets) from its two-dimensional image, drawing lines orthogonal to the longitudinal directions of the fibers, and directly reading the fiber diameters.

The above fiber, under the principle of its production, becomes an infinite-length continuous fiber, but it is preferable that the fiber have a length at least 100 or more times a thickness of the fiber. In the present description, a fiber having a length 100 or more times a thickness of the fiber is defined as a "continuous fiber". It is preferable that a coating produced by the electrostatic spray method be a porous discontinuous coating composed of a deposit of continuous fibers. The coating of such a form not only can be handled as one sheet as an aggregate, but also has a feature of being very soft, and has advantages of hardly falling into pieces even under a shearing force and being excellent in followability to movements of the body. The coating also has an advantage of being excellent in diffusibility of sweat generated from skin. The coating further also has an advantage of being easily peeled off. By contrast, a continuous coating having no pores is not easily peeled off and since the diffusibility of sweat is very low, easily causes stuffiness on skin.

The spraying composition having become fibrous reaches a skin, in a charged state. Since the skin is also charged as described before, the fibers adhere closely with the skin by an electrostatic force. Since fine irregularities such as texture are formed on the surface of skin, the fibers adhere more closely with the skin surface conjointly with the anchor effect by the irregularities. When the electrostatic spraying is thus completed, the power source of the electrostatic spray apparatus 10 is turned off. Thereby, the electric field between the nozzle and the skin vanishes and charges are immobilized on the skin surface. Consequently, the adhesiveness of the coating more develops.

Although the above description has been for a porous coating composed of a deposit of fibers as the coating, forms of coatings are not limited thereto; a continuous coating having no pores may be formed; or a porous coating having a form other than a deposit of fibers, for example, a porous coating made by irregularly or regularly forming a plurality of throughholes on a continuous coating, that is, a discontinuous coating may be formed. As described above, by controlling the viscosity of the spraying composition, the distance between the nozzle and a skin, the voltage applied to the nozzle, and the like, a coating having an optional shape can be formed.

It is preferable, for successfully forming a coating, that the distance between the nozzle and a skin is, though depending also on the voltage applied to the nozzle, 50 mm or more and 150 mm or less. The distance between the nozzle and a skin can be measured by a noncontact type sensor usually used, or the like.

Irrespective of whether or not a coating formed by the electrostatic spray method is porous, the basis weight of the coating is preferably 0.1 $g/m^2$ or more and more preferably 1 $g/m^2$ or more. The basis weight is preferably 30 $g/m^2$ or less and more preferably 20 $g/m^2$ or less. The basis weight of the coating is, for example, preferably 0.1 $g/m^2$ or more and 30 $g/m^2$ or less and more preferably 1 $g/m^2$ or more and 20 $g/m^2$ or less. By thus setting the basis weight of a coating, the adhesiveness of the coating can be improved. The electrostatic spray step of electrostatically spraying the composition directly on a skin to thereby form a coating means a step of carrying out electrostatic spraying on a skin to thereby form a coating. A step of electrostatically spraying a composition on a place other than a skin to form a sheet composed of fibers, and applying the sheet to a skin is different from the above electrostatic spray step.

Then, the step B will be described.

The step B is a step of applying, to the skin, the composition Y, other than the composition X (spraying composition), comprising the group consisting of a component (c) and a component (d). The step B is carried out before or after the electrostatic spray step A.

(c) 5% by mass or more and 20% by mass or less of an adhesive polymer, and (d) 1% by mass or more and 40% by mass or less of a polyol.

The step B is a step of applying the composition Y to a skin by using a unit other than electrostatic spraying.

The (c) adhesive polymer to be used for the composition Y contributes to the scratch resistance and the extensibility of the coating formed on the skin by the electrostatic spraying. As the adhesive polymer, there can be used ones usually used as an adhesive agent or a pressure-sensitive adhesive agent. Examples thereof include rubber-based adhesive polymers, silicone-based adhesive polymers, acrylic adhesive polymers and urethane-based adhesive polymers, and one or more selected therefrom can be used. Further as the (c) adhesive polymer, there can be used at least one selected from the group consisting of a nonionic polymer, an anionic polymer, a cationic polymer and an amphoteric polymer. It is preferable that the (c) adhesive polymer be a polymer other than a polymer of the component (b).

Examples of the rubber-based adhesive polymers include ones produced by using, as a base polymer, a natural rubber; a synthetic rubber such as polyisoprene rubber, styrene-butadiene (SB) rubber, styrene-isoprene (SI) rubber, styrene-isoprene-styrene block copolymer (SIS) rubber, styrene-butadiene-styrene block copolymer (SBS) rubber, styrene-ethylene-butylene-styrene block copolymer (SEGS) rubber, styrene-ethylene-propylene-styrene block copolymer (SEPS) rubber, styrene-ethylene-propylene block copolymer (SEP) rubber, reclaimed rubber, butyl rubber, polyisobutylene or a modified substance of these; or the like.

Among these rubber-based adhesive polymers, more preferable is at least one selected from the group consisting of a styrene-isoprene-styrene block copolymer, a styrene-butadiene-styrene block copolymer, a styrene-butadiene rubber, a polyisobutylene, a polyisoprene rubber and a silicone rubber. A commercially available product of the rubber-based adhesive polymer includes Yodosol GH41F (manufactured by Akzo Nobel N.V.).

Examples of the acrylic adhesive polymers include acrylic adhesive agents produced by using, as a base polymer, an acrylic polymer (homopolymer or copolymer) produced by using, as a monomer component, one or more alkyl (meth)acrylates. Specific examples of the alkyl (meth)acrylates include C1-20 alkyl (meth)acrylates such as methyl (meth)acrylate, ethyl (meth)acrylate, propyl (meth)acrylate, isopropyl (meth)acrylate, butyl (meth)acrylate, isobutyl (meth)acrylate, s-butyl (meth)acrylate, t-butyl (meth)acrylate, pentyl (meth)acrylate, hexyl (meth)acrylate, heptyl (meth)acrylate, octyl (meth)acrylate, 2-ethylhexyl (meth)acrylate, isooctyl (meth)acrylate, nonyl (meth)acrylate, isononyl (meth)acrylate, decyl (meth)acrylate, isodecyl (meth)acrylate, undecyl (meth)acrylate, dodecyl (meth)acrylate, tri- decyl (meth)acrylate, tetradecyl (meth)acrylate, pentadecyl (meth)acrylate, hexadecyl (meth)acrylate, heptadecyl (meth)acrylate, octadecyl (meth)acrylate, nonadecyl (meth) acrylate and eicosyl methacrylate.

Auxiliary monomers to be used together with these base polymers include N-vinylpyrrolidone, methylvinylpyrrolidone, (meth)acrylic acid and vinyl acetate. Commercially available products of the acrylic polymers include Amphomer 28-4910 (manufactured by Akzo Nobel N.V.), Yodosol GH256F (manufactured by Akzo Nobel N.V., particle diameter: 20 to 40 nm), Yodosol GH800F (manufactured by Akzo Nobel N.V.), Yodosol GH810F (manufactured by Akzo Nobel N.V.), Daitosol 5000AD (manufactured by Daito Kasei Kogyo Co., Ltd.) and Daitosol 5000SJ (manufactured by Daito Kasei Kogyo Co., Ltd.).

As the silicone-based adhesive polymer, there is preferably used, for example, a silicone-based adhesive agent produced by using, as a base polymer, a silicone rubber or silicone resin containing organopolysiloxane. As the base polymer constituting the silicone-based adhesive agent, there may be used a base polymer produced by crosslinking the silicone rubber or silicone resin. Examples of the silicone rubber include organopolysiloxanes containing dimethylsiloxane as their constituting unit. To the organopolysiloxanes, as required, a functional group (for example, a vinyl group) may be introduced. Examples of the silicone resin include organopolysiloxanes containing, as their constituting unit, at least one constituting unit selected from the group consisting of an $R_3SiO_{1/2}$ constituting unit, a $SiO_2$ constituting unit, an $RSiO_{3/2}$ constituting unit and an $R_2SiO$ constituting unit. The silicone-based pressure-sensitive adhesive polymer may contain a crosslinking agent. Examples of the crosslinking agent include siloxane-based crosslinking agents and peroxide-based crosslinking agents. As the peroxide-based crosslinking agent, an optional suitable one can be used. Examples of the peroxide-based crosslinking agent include benzoyl peroxide, t-butyl peroxybenzoate and dicumyl peroxide. Examples of the siloxane-based crosslinking agent include polyorganohydrogensiloxane.

As the organopolysiloxane, there can be used the following poly(N-acylalkyleneimine)-modified organopolysiloxane (hereinafter, referred to also simply as "modified organopolysiloxane").

The modified organopolysiloxane is one made by binding a poly(N-acylalkyleneimine) segment composed of a repeating unit represented by the following general formula (1):

(1)

in the formula, $R^1$ denotes a hydrogen atom, an alkyl group having 1 to 22 carbon atoms, an aralkyl group or an aryl group, to at least two silicon atoms of an organopolysiloxane segment constituting its main chain, through an alkylene group containing a heteroatom, wherein in the modified organopolysiloxane, the mass ratio of the organopolysiloxane segment (α) constituting its main chain and the poly(N-acylalkyleneimine) segment (β), (α/β), is 40/60 or more and 98/2 or less; and the weight-average molecular weight of the organopolysiloxane segment constituting its main chain is 30,000 or more and 100,000 or less.

The mass ratio of the organopolysiloxane segment (α) and the poly(N-acylalkyleneimine) segment (β), (α/β), in the modified organopolysiloxane is, from the viewpoint of improving friction resistance of a coating, preferably 40/60 or more, more preferably 55/45 or more and even more preferably 65/35 or more. Further, the ratio is, from the viewpoint of forming a coating in a fibrous form, preferably 98/2 or less, more preferably 90/10 or less and even more preferably 82/18 or less.

In the modified organopolysiloxane, although at least two poly(N-acylalkyleneimine) segments can be bound to any silicon atoms constituting the organopolysiloxane segment through an alkylene group containing a heteroatom, it is preferable that the poly(N-acylalkyleneimine) segment be bound to one or more silicon atoms excluding ones on both the terminals through the above alkylene group, and it is more preferable that the poly(N-acylalkyleneimine) segments are bound to two or more silicon atoms excluding ones on both the terminals through the above alkylene group.

The alkylene group containing a heteroatom intervening in the binding of the organopolysiloxane segment and the poly(N-acylalkyleneimine) includes alkylene groups having 2 to 20 carbon atoms containing 1 to 3 nitrogen atoms, oxygen atoms and/or sulfur atoms. Specific examples thereof include the following.

[in the formulae, An⁻ denotes an anion.]

An N-acylalkyleneimine unit constituting the poly(N-acylalkyleneimine) segment is represented by the above general formula (1); in the general formula (1), examples of the alkyl group having 1 to 22 carbon atoms of $R^1$ include straight-chain, branched or cyclic alkyl groups having 1 to 22 carbon atoms; and specific examples thereof include a methyl group, an ethyl group, an n-propyl group, an isopropyl group, an n-butyl group, a tert-butyl group, a pentyl group, a hexyl group, a cyclohexyl group, a heptyl group, an octyl group, a nonyl group, a decyl group, an undecyl group, a dodecyl group, an octadecyl group, a nonadecyl group, an eicosyl group and a docosyl group.

Examples of the aralkyl group include aralkyl groups having 7 to 15 carbon atoms, and specific examples thereof include a benzyl group, a phenethyl group, a trityl group, a naphthylmethyl group and an anthracenylmethyl group.

Examples of the aryl group include aryl groups having 6 to 14 carbon atoms, and specific examples thereof include a phenyl group, a tolyl group, a xylyl group, a naphthyl group, a biphenyl group, an anthryl group and a phenanthryl group.

Here, in the present description, the mass ratio ($\alpha/\beta$) refers to a value obtained by dissolving a modified organopolysiloxane in 5% by mass in heavy chloroform, subjecting the solution to a nuclear magnetic resonance ($^1$H-NMR) analysis, and determining an integral ratio of an alkyl group or a phenyl group in organopolysiloxane segments to a methylene group in poly(N-acylalkyleneimine) segments.

In the modified organopolysiloxane, the weight-average molecular weight (MWg) of an organopolysiloxane segment between neighboring poly(N-acylalkyleneimine) segments is preferably 1,300 or more, more preferably 1,500 or more and even more preferably 1,800 or more, and preferably 32,000 or less, more preferably 10,000 or less and even more preferably 5,000 or less.

In the present description, the "organopolysiloxane segment between neighboring poly(N-acylalkyleneimine) segments" is, as represented in the following formula (2), a moiety encircled by dashed lines between two points from a binding point (binding point A) of an organopolysiloxane segment with a poly(N-acylalkyleneimine) segment to a binding point (binding point B) of the organopolysiloxane segment with a neighboring poly(N-acylalkyleneimine) segment, and refers to a segment constituted of one $R^2SiO$ unit, one $R^6$ and (y+1) $R^2{}_2SiO$ units. Further, the "poly(N-acylalkyleneimine) segment" refers to —Z—$R^7$ bound to the above $R^6$.

(2)

In the general formula (2), $R^2$ each independently denote an alkyl group having 1 to 22 carbon atoms or a phenyl group; $R^6$ denotes an alkylene group containing a heteroatom; $R^7$ denotes a residue of a polymerization initiator; —Z—$R^7$ denotes a poly(N-acylalkyleneimine) segment; and y denotes a positive number.

The MWg, though being a molecular weight of the moiety encircled by dashed lines in the above general formula (2), can be interpreted as a mass (g/mol) of organopolysiloxane segments per 1 mol of poly(N-acylalkyleneimine) segments, and when 100% of functional groups of an organopolysiloxane serving as a raw material compound is substituted by the poly(N-acylalkyleneimine), coincides with the functional group equivalent weight (g/mol) of a modified organopolysiloxane.

In the case where the functional group equivalent weight (g/mol) of the organopolysiloxane serving as a raw material compound has already been known, the MWg, even in the case where 100% of the functional groups is not substituted by the poly(N-acylalkyleneimine), can be calculated by the following expression.

MWg=[a functional group equivalent weight (g/mol) of an organopolysiloxane]/[a substitution rate (%)/100(%)]

Further in the case where the functional group equivalent weight of the organopolysiloxane is not known, the MWg can be determined by the following expression by using a content rate (Csi) of the organopolysiloxane segment constituting the main chain and a molecular weight (MWox) of the poly(N-acylalkyleneimine) segment.

$$MWg = \frac{Csi \times MWox}{100 - Csi}$$

The molecular weight (MWox) of the poly(N-acylalkyleneimine) segment can be calculated from a molecular weight and a degree of polymerization of the N-acylalkyleneimine unit, or can be measured by a gel permeation chromatography (GPC) method described later, but in the present invention, refers to a number-average molecular weight measured by the GPC method. The MWox of the modified organopolysiloxane is, from the viewpoint of excellence in friction resistance, preferably 500 or more, more preferably 600 or more and even more preferably 700 or more, and preferably 5,500 or less, more preferably 3,500 or less and even more preferably 3,000 or less.

The weight-average molecular weight (MWsi) of the organopolysiloxane segment constituting the main chain is, from the viewpoint of excellence in friction resistance, preferably 7,000 or more, more preferably 10,000 or more and even more preferably 20,000 or more, and preferably 120,000 or less, more preferably 80,000 or less and even more preferably 60,000 or less. Since the organopolysiloxane segment constituting the main chain has a skeleton common to that of the organopolysiloxane serving as the raw material compound, the MWsi is nearly equal to the weight-average molecular weight of the organopolysiloxane serving as the raw material compound. Here, the weight-average molecular weight of the organopolysiloxane serving as the raw material compound is measured by GPC in terms of polystyrene under the following condition.

Column: Super HZ4000+Super HZ2000 (manufactured by Tosoh Corp.)
Eluate: 1-mM trimethylamine/THF
Flow volume: 0.35 mL/min
Column temperature: 40° C.
Detector: UV
Sample: 50 μL The weight-average molecular weight (MWt) of the modified organopolysiloxane is preferably 10,000 or more, more preferably 12,000 or more and even more preferably 24,000 or more, and then preferably 200,000 or less, more preferably 150,000 or less, even more preferably 120,000 or less, further more preferably 92,000 or less and further more preferably 80,000 or less. Thereby, a coating is made which has a sufficient coating strength and is excellent in friction resistance. In the present description, the MWt can be determined from the weight-average molecular weight of the modified organopolysiloxane serving as the raw material compound and the above-mentioned mass ratio ($\alpha/\beta$).

The modified organopolysiloxane can be produced by a well-known production method including, for example, methods disclosed in JP-A-2009-024114 and WO2011/062210.

The urethane-based pressure-sensitive adhesive polymer includes ones composed of a urethane resin obtained by reacting a polyol with a polyisocyanate compound. Examples of the polyol include polyether polyols, polyester polyols, polycarbonate polyols and polycaprolactone polyols. Examples of the polyisocyanate compounds include diphenylmethane diisocyanate, tolylene diisocyanate and hexamethylene diisocyanate. Commercially available products of the urethane-based adhesive polymers include Baycusan $C_{1004}$ (manufactured by Covestro AG).

The nonionic polymers are not especially limited, and any thereof can be used as long as they are usually used in the cosmetic field. One or more of nonionic polymers can be contained in the above composition Y, and one or more of anionic, cationic and/or amphoteric polymers can be contained in combination with the nonionic polymers.

Examples of the nonionic polymers include (meth)acrylic water-soluble nonionic polymers, (meth)acrylic water-insoluble nonionic polymers, polyvinylpyrrolidone, polyacrylamide, low-saponified polyvinyl alcohols (degree of saponification: 60 mol % or less), neutral polysaccharides and derivatives thereof (ethers, esters and the like thereof), and polyether. The neutral saccharides and derivatives thereof include neutral gums (guar gum, hydroxypropyl guar and the like), cellulose ethers (hydroxyethylcellulose (HEC), methylhydroxyethylcellulose (MHEC), ethylhydroxyethylcellulose (EHEC), methylethylhydroxyethylcellulose (MEHEC), hydroxypropylcellulose (HPC), hydroxypropylmethylcellulose (HPMC) and hydrophobized derivatives thereof (HM-EHEC and the like), and starches and derivatives thereof (dextrin and the like). The polyether include polyethylene glycol and polypropylene glycol.

Hereinafter, there are, cited examples of compounds having an ethylenic unsaturated bond which can constitute the above-mentioned nonionic polymers such as (meth)acrylic water-soluble nonionic polymers, (meth)acrylic water-insoluble nonionic polymers, polyvinylpyrrolidone, polyacrylamide and low-saponified polyvinyl alcohols (degree of saponification: 60 mol % or less), but the present invention is not any more limited to the following specific examples.

Examples of nonionic monomers include (meth)acrylate esters such as methyl (meth)acrylate, ethyl (meth)acrylate, n-propyl (meth)acrylate, isopropyl (meth)acrylate, n-butyl (meth)acrylate, isobutyl (meth)acrylate, t-butyl (meth)acrylate, n-pentyl (meth)acrylate, n-hexyl (meth)acrylate, cyclohexyl (meth)acrylate, n-heptyl (meth)acrylate, n-octyl (meth)acrylate, 2-ethylhexyl (meth)acrylate, nonyl (meth)acrylate, decyl (meth)acrylate, dodecyl (meth)acrylate, phenyl (meth)acrylate, toluyl (meth)acrylate, benzyl (meth)acrylate), isobornyl (meth)acrylate, 2-methoxyethyl (meth)acrylate, 3-methoxybutyl (meth)acrylate, 2-hydroxyethyl (meth)acrylate, 2-hydroxypropyl (meth)acrylate, stearyl (meth)acrylate, glycidyl (meth)acrylate, 2-aminoethyl (meth)acrylate, γ-((meth)acryloyloxypropyl)trimethoxysilane, γ-((meth)acryloyloxypropyl)dimethoxymethylsilane, ethylene oxide adducts of (meth)acrylic acid, trifluoromethylmethyl (meth)acrylate, 2-trifluoromethylethyl (meth)acrylate, 2-perfluoroethylethyl (meth)acrylate, 2-perfluoroethyl-2-perfluorobutylethyl (meth)acrylate, 2-perfluoroethyl (meth)acrylate, perfluoromethyl (meth)acrylate, diperfluoromethylmethyl (meth)acrylate, 2-perfluoromethyl-2-perfluoroethylmethyl (meth)acrylate, 2-perfluorohexylethyl (meth)acrylate, 2-perfluorodecylethyl (meth)acrylate and 2-perluorohexadecylethyl (meth)acrylate; aromatic alkenyl compounds such as styrene, α-methylstyrene, p-methylstyrene and p-methoxystyrene; cyanated vinyl compounds such as acrylonitrile and methacrylonitrile; conjugated dienic compounds such as butadiene and isoprene; halogen-containing unsaturated compounds such as vinyl chloride, vinylidene chloride, perfluoroethylene, perfluoropropylene and vinylidene fluoride; silicon-containing unsaturated compounds such as vinyltrimethoxysilane and vinyltriethoxysilane; unsaturated carboxylic anhydrides such as maleic anhydride; unsaturated dicarboxylate diesters such as dialkyl maleate and dialkyl fumarate; vinyl ester compounds such as vinyl acetate, vinyl propionate, vinyl pivalate, vinyl benzoate and vinyl cinnamate; maleimide compounds such as maleimide, N-methylmaleimide, N-ethylmaleimide, N-propylmaleimide, N-butylmaleimide, N-hexylmaleimide, N-octylmaleimide, N-dodecylmaleimide, N-stearylmaleimide, N-phenylmaleimide and N-cyclohexylmaleimide; monomers derived from (meth)acrylic acid or (meth)acrylamide and an alkylene oxide having 2 to 4 carbon atoms, such as polyethylene glycol (meth)acrylate, methoxypoly (ethylene glycol/propylene glycol) mono-(meth)acrylate, polyethylene glycol di(meth)acrylate and N-polyalkyleneoxy(meth)acrylamide; and hydrophilic nonionic monomers such as N-vinylpyrrolidone, N-(meth)acryloylmorpholine and acrylamide.

Among these, preferable is one or more selected from the group consisting of a (meth)acrylic water-insoluble nonionic polymer, polyvinylpyrrolidone and a low-saponified polyvinyl alcohol (degree of saponification: 60 mol % or less). Examples of commercially available products thereof include MAS 683 (manufactured by CosMED Pharmaceutical Co., Ltd.), Polyvinylpyrrolidone K-90 (manufactured by BASF AG) and JMR-150L (manufactured by Japan VAM & Poval Co., Ltd.).

Here, in the present description, the expression of "(meth) acryl" means "acryl or methacryl".

The anionic polymers are not especially limited, and there can be used any thereof as long as they are usually used in the cosmetic field. The above-mentioned liquid agent can comprise one or more anionic polymers, and can further comprise one or more nonionic, cationic and/or amphoteric polymers in combination with the anionic polymers.

Examples of the anionic polymers include anionic polysaccharides and derivatives thereof (alginate salts, pectin, hyaluronate salts and the like), anionic gums (xanthan gum, dehydroxanthan gum, hydroxypropylxanthan gum, gum arabic, karaya gum, gum tragacanth and the like), anionic cellulose derivatives (carboxymethylcellulose (CMC) and the like), (meth)acrylic water-soluble anionic polymers and acrylamide-based water-soluble anionic polymers.

Hereinafter, there are cited examples of compounds having an ethylenic unsaturated bond which can constitute the above-mentioned anionic polymers such as the (meth) acrylic water-soluble anionic polymers, but the present invention is not any more limited to the following specific examples. Examples of anionic monomers include unsaturated carboxylic acid compounds such as (meth)acrylic acid, maleic acid, maleic anhydride, itaconic acid, fumaric acid and crotonic acid; partial ester compounds of an unsaturated polybasic acid anhydride (for example, succinic anhydride or phthalic anhydride) with a hydroxyl-containing (meth) acrylate (for example, hydroxyethyl (meth)acrylate); compounds having a sulfonate group, such as styrenesulfonic acid and sulfoethyl (meth)acrylate; and compounds having a phosphate group, such as acid phosphooxyethyl (meth) acrylate. These anionic unsaturated monomers can be used as acids as they are, or by being partially neutralized or by being completely neutralized; or the anionic unsaturated monomers can also be partially neutralized or completely neutralized after being provided as acids as they are for copolymerization. Examples of basic compounds to be used for the neutralization include alkali metal hydroxides such as potassium hydroxide and sodium hydroxide, ammonia water, and amine compounds such as mono-, di- and tri-ethanolamines and trimethylamine.

Among these, acrylic water-insoluble anionic polymers are especially preferable. Examples of commercially available products thereof include MASCOS 10 (manufactured by CosMED Pharmaceutical Co., Ltd.) and HiPAS 10 (manufactured by CosMED Pharmaceutical Co., Ltd.).

Further there can also be used an emulsifying thickener containing these nonionic polymer and anionic polymer. Examples thereof include
Polyacrylamide/(C13,C14)Isoparafin/Laureth-7 (Sepigel 305, manufactured by Seppic).

The cationic polymers are not especially limited, and there can be used any thereof as long as they are usually used in the cosmetic field. The above-mentioned liquid agent can comprise one or more cationic polymers, and can further comprise one or more nonionic, anionic and/or amphoteric polymers in combination with the cationic polymers.

The cationic polymer is a polymer having a cationic group such as a quaternary ammonium group, or a group such as a primary, secondary or tertiary amino group, which can be ionized to a cationic group. The cationic polymer is typically a polymer having an amino group or an ammonium group on the side chain of the polymer chain, or a polymer containing a diallyl quaternary ammonium salt as its constituting unit.

Examples of preferable cationic polymers include cationized cellulose, cationic starch, cationic guar gum, vinylic or (meth)acrylic polymer or copolymers thereof having a quaternary ammonium side chain, quaternized polyvinylpyrrolidone, (meth)acrylate/aminoacrylate copolymers, amine-substituted poly(meth)acrylate cross polymers, (meth)acrylic water-soluble cationic polymers and acrylamide-based water-soluble cationic polymers.

Hereinafter, there are cited examples of compounds having an ethylenic unsaturated bond which can constitute the above-mentioned cationic polymers such as the (meth) acrylic water-soluble cationic polymers, but the present invention is not any more limited to the following specific examples. Examples of cationic monomers include ones made by cationizing N,N-dimethylaminoethyl (meth)acrylate, N,N-diethylaminoethyl (meth)acrylate, N,N-dimethylaminopropyl (meth)acrylate, N,N-diethylaminopropyl (meth)acrylate, N,N-dimethylaminoethyl (meth)acrylamide, N,N-diethylaminoethyl (meth)acrylamide, N,N-dimethylaminopropyl (meth)acrylamide, N,N-diethylaminopropyl (meth)acrylamide, p-dimethylaminomethylstyrene, p-dimethylaminoethylstyrene, p-diethylaminomethylstyrene, p-diethylaminoethylstyrene or the like, with a cationizing agent (for example, a halogenated alkyl such as methyl chloride, methyl bromide or methyl iodide, a dialkylsulfuric acid such as dimethylsulfuric acid, an epichlorohydrin adduct of a tertiary amine mineral acid salt such as N-(3-chloro-2-hydroxypropyl)-N,N,N-trimethylammonium chloride, an inorganic salt of hydrochloric acid, hydrobromic acid, sulfuric acid, phosphoric acid or the like, or a carboxylic acid such as formic acid, acetic acid or propionic acid).

Specific examples of the cationized cellulose include a polymer (polyquaternium-10) of a quaternary ammonium salt obtained by adding glycidyltrimethylammonium chloride to hydroxyethylcellulose, a hydroxyethylcellulose/dimethyldiallylammonium chloride copolymer (polyquaternium-4), and a polymer (polyquaternium-67) of a quaternary ammonium salt obtained by reacting hydroxyethylcellulose with a trimethylammonium-substituted epoxide and a lauryldimethylammonium-substituted epoxide.

Examples of the vinylic or (meth)acrylic polymers or copolymers thereof having a quaternary ammonium side chain include poly(2-methacryloxyethyltrimethylammonium chloride) (polyquaternium-37).

Specific examples of the quaternized polypyrrolidone include a quaternary ammonium salt (polyquaternium-11) synthesized from a copolymer of vinylpyrrolidone (VP) with dimethylaminoethyl methacrylate, and diethyl sulfate.

Examples of the (meth)acrylate/aminoacrylate copolymer include an (acrylate/aminoacrylate/$C_{10}$-30 alkyl PEG-20 itaconic acid) copolymer.

Examples of the amine-substituted poly(meth)acrylate cross polymer include a polyacrylate-1 cross polymer and polyquaternium-52.

Among these, the acrylamide-based water-soluble cationic polymers are especially preferable. Examples of commercially available products thereof include a t-butylacrylamide/ethyl acrylate/dimethylaminopropylacrylamide/methoxypolyethylene glycol (meth)acrylate copolymer (RP77S, manufactured by Kao Corp.).

The amphoteric polymer is a polymer having both a cationic group and an anionic group. Speaking from the structural viewpoint, the amphoteric polymer can be derived by introducing an anionic group or a comonomer having an anionic group to any one of the above-mentioned cationic polymers.

There can be used any of the amphoteric polymers as long as they are usually used in the cosmetic field. The above-mentioned liquid agent can comprise one or more amphoteric polymers, and can further comprise nonionic, anionic and/or cationic polymers in combination with the amphoteric polymers.

Examples of the amphoteric polymers include carboxyl-modified or sulfonate-modified cationic polysaccharides (carboxymethylchitosan and the like), (meth)acrylate-based polymers having a phosphobetaine group or a sulfobetaine group on their side chain, and (meth)acrylic amphoteric polymers.

Hereinafter, there are cited examples of compounds having an ethylenic unsaturated bond which can constitute the above-mentioned amphoteric polymers such as the (meth) acrylic amphoteric polymers, but the present invention is not any more limited to the following specific examples. Examples of amphoteric monomers include compounds obtained by causing a modifying agent such as sodium or potassium haloacetate to act on an above-mentioned specific example of the cationic monomer precursors. Further, specific examples of polarizing monomers include oxidized amine compounds of N,N-dimethylaminoethyl (meth)acrylate, N,N-diethylaminoethyl (meth)acrylate, N,N-dimethylaminopropyl (meth)acrylate, N,N-diethylaminopropyl (meth)acrylate, N,N-dimethylaminoethyl(meth)acrylamide, N,N-diethylaminoethyl(meth)acrylamide, N,N-dimethylaminopropyl(meth)acrylamide, N,N-diethylaminopropyl (meth)acrylamide, N,N-dimethylaminovinyl propionate, p-dimethylaminomethylstyrene, p-dimethylaminoethylstyrene, p-diethylaminomethylstyrene, p-diethylaminoethylstyrene or the like.

Other examples thereof include copolymers (dimethylallylammonium chloride/acrylic acid copolymer (polyquaternium-22) and the like) of a cationic vinylic or (meth)acrylic monomer with (meth)acrylic acid.

As the (c) adhesive polymer, from the viewpoint of improving the scratch resistance and the extensibility of the coating, an adhesive polymer good in adhesiveness is selected. As the adhesive polymer, a polymer is preferable which has a maximum tensile shearing load of 1 N or more as measured by reference to JIS K6850; a polymer of 3 N or more is more preferable; and a polymer of 5 N or more is even more preferable. Further from the viewpoint of securing adhesiveness, a polymer of 8 N or more is further more preferable. The maximum tensile shearing load is preferably 200 N or less, more preferably 150 N or less and even more preferably 100 N or less. Specifically, it is preferable to use one or more selected from the group consisting of the rubber-based adhesive polymer, the silicone-based adhesive polymer, the acrylic adhesive polymer and the urethane-based adhesive polymer; and then, it is preferable to use at least one selected from the group consisting of the nonionic polymer, the anionic polymer, the cationic polymer and the amphoteric polymer.

The adhesiveness (maximum tensile shearing load) of the polymer can be measured as follows. 20 mg of a polymer solution (a 10% ethanol solution, a saturated ethanol solution or a saturated aqueous solution) is applied to a region of 1.25 cm×2.5 cm of one end of one sheet of a polycarbonate substrate (manufactured by Standard Test Piece, Carboglass Polish Clear, 10 cm×2.5 cm×2.0 cm), and laminated with another sheet of the polycarbonate substrate, and dried for 12 or more hours. Both ends of the polycarbonate substrates were pulled by using a Tensilon UTC-100W, manufactured by Orientec Co., Ltd. at a tensile rate of 5 mm/min to measure the maximum tensile shearing load.

The content of the (c) adhesive polymer in the composition Y is, from the viewpoint of the scratch resistance and the extensibility of the coating, 5% by mass or more and 20% by mass or less. The content is more preferably 6% by mass or more. Then the content is more preferably 15% by mass or less, even more preferably 12% by mass or less and further more preferably 10% by mass or less. Specifically, the content is preferably 5% by mass or more and 15% by mass or less, more preferably 5% by mass or more and 12% by mass or less and further more preferably 5% by mass or more and 10% by mass or less.

The component (d) to be used for the composition Y is a polyol. Examples of the polyol include alkylene glycols such as ethylene glycol, propylene glycol, 1,3-propanediol and 1,3-butanediol; polyalkylene glycols such as diethylene glycol, dipropylene glycol, and polyethylene glycol and polypropylene glycol having a weight-average molecular weight of 1,000 or less; and glycerols such as glycerol, diglycerol and triglycerol. Among these, from the viewpoint of the scratch resistance and the extensibility of the coating, preferable are ethylene glycol, propylene glycol, 1,3-butanediol, dipropylene glycol, polyethylene glycol having a weight-average molecular weight of 1,000 or less, glycerol and diglycerol; and more preferable are propylene glycol, 1,3-butanediol and glycerol; and even more preferable are glycerols.

The content of the component (d) in the composition Y is, from the viewpoint of the scratch resistance and the extensibility of the coating, preferably 1% by mass or more and 40% by mass or less, more preferably 1% by mass or more and 30% by mass or less, even more preferably 3% by mass or more and 25% by mass or less, further more preferably 5% by mass or more and 20% by mass or less and further more preferably 10% by mass or more and 20% by mass or less.

The mass proportion of the component (d) to the component (c) in the composition Y, ((d)/(c)), is, from the viewpoint of the scratch resistance and the extensibility of the coating, preferably 0.1 or more and 8 or less, more preferably 0.2 or more and 7 or less and even more preferably 0.3 or more and 6 or less.

The composition Y can further comprise a component (e), an oil. The incorporation of the component (e) more improves the scratch resistance and the extensibility of a coating, stable fixation of solid materials and followability of the coating to movements of skin. The component (e) includes one or more selected from the group consisting of a liquid oil (an oil liquid at 20° C.) and a solid oil (an oil solid at 20° C.)

The liquid oil in the present invention is an oil liquid at 20° C., and includes semi-solid ones having flowability. The liquid oil includes hydrocarbon oils, ester oils, higher alcohols, silicone oils and fatty acids. Among these, from the viewpoint of smoothness in application, friction resistance and extensibility of a coating, preferable are hydrocarbon oils, ester oils and silicone oils. Further one or more, in combination, selected from these liquid oils may be used.

The liquid hydrocarbon oil includes liquid paraffin, squalane, squalene, n-octane, n-heptane, cyclohexane, light isoparaffin, liquid isoparaffin, hydrogenated polyisobutene, polybutene and polyisobutene; and from the viewpoint of usage feeling, preferable are liquid paraffin, light isoparaffin, liquid isoparaffin, squalane, squalene, n-octane, n-heptane and cyclohexane; and more preferable are liquid paraffin and squalene. The viscosity at 30° C. of the hydrocarbon oil is, from the viewpoint of scratch resistance and extensibility of an electrostatically sprayed coating, preferably 1 mPa·s or more and more preferably 3 mPa·s or more. Then the content of the total of isodecane, isohexadecane and hydrogenated polyisobutene in the liquid agent is, from the viewpoint of scratch resistance and extensibility of a coating, preferably 10% by mass or less, more preferably 5% by mass or less, even more preferably 1% by mass or less and further more preferably 0.5° by mass or less; and the liquid agent may not contain these.

The viscosity at 30° C. of the ester oil and the silicone oil is, similarly from the viewpoint of scratch resistance and extensibility of an electrostatically sprayed coating, preferably 1 mPa·s or more and more preferably 3 mPa·s or more.

The viscosity used here is measured at 30° C. by a BM-type viscometer (manufactured by Tokyo Keiki Inc., measuring condition: rotor, No. 1, 60 rpm, for 1 min). From the similar viewpoint, the content of the total of the ether oils such as cetyl-1,3-dimethylbutyl ether, dicapryl ether, dilauryl ether and diisostearyl ether in the liquid agent is preferably 10° by mass or less, more preferably 5% by mass or less and even more preferably 1% by mass or less.

The ester oils include esters composed of a straight-chain or branched-chain fatty acid and a straight-chain or branched-chain alcohol or polyhydric alcohol. Specific examples thereof include isopropyl myristate, cetyl isooctanoate, isocetyl octanoate, octyldodecyl myristate, isopropyl palmitate, butyl stearate, hexyl laurate, decyl oleate, octyldodecyl oleate, hexyldecyl dimethyloctanoate, cetyl lactate, myristyl lactate, lanolin acetate, isocetyl stearate, isocetyl isostearate, ethylhexyl isononanoate, isononyl isononanoate, isotridecyl isononanoate, isostearyl isostearate, cholesteryl 12-hydroxystearate, ethylene glycol di-2-ethylhexanoate, a dipentaerythritol fatty acid ester, N-alkyl glycol mono-isostearate, propylene glycol dicaprylate, propylene glycol diisostearate, neopentyl glycol dicaprylate, diisostearyl malate, glycerol di-2-heptylundecanoate, trimethylolpropane tri-2-ethylhexanoate, trimethylolpropane triisostearate, pentaerythrit tetra-2-ethylhexanoate, glyceryl tri-2-ethylhexanoate, trimethylolpropane triisostearate, cetyl 2-ethylhexanoate, 2-ethylhexyl palmitate, diethylhexyl naphthalenedicarboxylate, C12 to 15 alkyl benzoate, stearyl isononanoate, glyceryl tri(caprylate/caprate), butylene glycol (dicaprylate/caprate), propylene glycol di(caprylate/caprate), glyceryl triisostearate, glyceryl tri-2-heptylundecanoate, a tri-coconut oil fatty acid glyceryl ester, a castor oil fatty acid methyl ester, oleyl oleate, 2-heptylundecyl palmitate, diisobutyl adipate, an N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, di-2-ethylhexyl succinate, triethyl citrate, 2-ethylhexyl paramethoxycinnamate and tripropylene glycol dipivalate.

Among these, from the viewpoint of making an electrostatically sprayed coating to closely adhere on a skin and excellence in feeling when the coating is applied to the skin, preferable is one selected from the group consisting of octyldodecyl myristate, myristyl myristate, isocetyl stearate, isononyl isononanoate, isocetyl isostearate, stearyl isononanoate, diisobutyl adipate, di-2-ethylhexyl sebacate, isopropyl myristate, isopropyl palmitate, diisostearyl malate, neopentylglycol dicaprate and glycerol tri(caprylate/caprate); more preferable is at least one selected from the group consisting of isopropyl myristate, isopropyl palmitate, diisostearyl malate, neopentyl glycol dicaprate, C12-15 alkyl benzoate and glycerol tri(caprylate/caprate); and even more preferable is at least one selected from the group consisting of neopentylglycol dicaprate and glycerol tri (caprylate/caprate).

As the ester oils, there can be used vegetable oils and animal oils containing the above ester oils; and examples thereof include olive oil, jojoba oil, macadamia nut oil, meadowfoam oil, castor oil, safflower oil, sunflower seed oil, avocado oil, canola oil, apricot kernel oil, rice embryo oil and rice bran oil.

The higher alcohols include liquid higher alcohols having 12 to 20 carbon atoms; preferable are higher alcohols containing a branched fatty acid as a constituent; and the higher alcohols specifically include isostearyl alcohol and oleyl alcohol.

The liquid silicone oils include straight-chain silicones, cyclic silicones and modified silicones, and examples thereof include dimethylpolysiloxane, dimethylcyclopolysiloxane, methylphenylpolysiloxane, methylhydrogenpolysiloxane, phenyl-modified silicones and higher alcohol-modified organopolysiloxanes. The content of the silicone oil in the component (d) is, from the viewpoint of adhesiveness to skin, preferably 35% by mass or less, and is, from the viewpoint of improving peelability, more preferably 10% by mass or less, even more preferably 1% by mass or less and further more preferably 0.1% by mass or less.

The kinematic viscosity at 25° C. of the silicone oil is, from the viewpoint of friction resistance of an electrostatically sprayed coating, fixation of solid materials and followability of the coating to movements of skin, preferably 3 mm$^2$/s or more, more preferably 4 mm$^2$/s or more and even more preferably 5 mm$^2$/s or more, and preferably 30 mm$^2$/s or less, more preferably 20 mm$^2$/s or less and even more preferably 10 mm$^2$/s or less.

Among these, from the viewpoint of friction resistance of an electrostatically sprayed coating, fixation of solid materials and followability of the coating to movements of skin, it is preferable that the silicone oil contain dimethylpolysiloxane.

Further, an oil solid at 20° C. (solid oil) also can be used. The oil solid at 20° C. exhibits a property of solid at 20° C., and one having a melting point of 40° C. or more is preferable. The oil solid at 20° C. includes hydrocarbon waxes, ester waxes, paraoxybenzoate esters, higher alcohols, esters of straight-chain fatty acid having 14 or more carbon atoms, triglycerides containing three straight-chain fatty acids having 12 or more carbon atoms as constituents and silicone waxes; and the solid oil can contain one or more selected from these. Such waxes are not limited as long as they are used for usual cosmetics; and examples thereof include mineral waxes such as ozokerite and ceresin; petroleum waxes such as paraffin, microcrystalline waxes and petrolatum; synthetic hydrocarbon waxes such as Fischer-Tropsh waxes and polyethylene waxes; vegetable waxes such as carnauba wax, candellila wax, rice wax, Japan wax, sunflower wax and hydrogenated jojoba oil; animal waxes such as beeswax and whale wax; synthetic waxes such as silicone wax, fluorine-based wax and synthetic beeswax; and fatty acids, higher alcohols and derivatives thereof. Further the paraoxybenzoate esters include methyl paraoxybenzoate, ethyl paraminobenzoate, isobutyl paraoxybenzoate, isopropyl paraoxybenzoate, ethyl paraoxybenzoate, butyl paraoxybenzoate, propyl paraoxybenzoate and benzyl paraoxybenzoate; and the triglycerides containing three straight-chain fatty acids having 12 or more carbon atoms as constituents include glyceryl trilaurate, glyceryl trimyristate, glyceryl tripalmitate and glyceryl tribehenate. The fatty acid ester oils having straight-chain fatty acid having 14 or more carbon atoms as constituents include myristyl myristate.

The content of the component (e) in the composition Y is, from the viewpoint of the scratch resistance and the extensibility of the coating and usage feeling, preferably 1% by mass or more and 20% by mass or less, more preferably 2% by mass or more and 18% by mass or less and even more preferably 3% by mass or more and 16% by mass or less.

The mass proportion of the component (e) to the component (c) in the composition Y, ((e)/(c)), is, from the viewpoint of the scratch resistance and the extensibility of the coating, preferably 0.06 or more and 4 or less, more preferably 0.07 or more and 3.5 or less and even more preferably 0.08 or more and 3 or less.

The composition Y may comprise, in addition to the above components, a surfactant, water-soluble polymers, a pH regulator, a chelating agent, a thickener, a fragrance, a coloring matter, a blood circulation accelerator, a cool sensation agent, an antiperspirant, a skin activator, a moisturizer, a refrigerant, a UV protective agent, a repellant, an antioxidant, a stabilizer, various vitamins, ethanol, and the like. The surfactant includes nonionic surfactants, cationic surfactants, anionic surfactants and amphoteric surfactants. The form of the composition Y may be an oil-in-water type emulsion composition or may be a water-in-oil type emulsion composition, but from the viewpoint of the scratch resistance and the extensibility of the coating, an oil-in-water type emulsion composition is preferable.

The step (step B) of applying the composition Y to a skin may be before or after the step A. A unit of applying the composition Y to a skin may be any unit as long as being a unit other than electrostatic spraying. The unit includes a unit of applying to a skin by a finger or the like, and a unit of applying to a skin by using an applicator.

The skin can also be made up by applying a cosmetic containing a powder to the skin (step C) before, between or after the step A and the step B. The steps can be carried out, for example, in the order of the step A, the step B and the step C; or in the order of the step B, the step A and the step C. Further the step A) can be carried out multiple times, and the steps can be carried out, for example, in the order of the step B, the step A, the step C, the step A and the step B. It is preferable that also the step C be carried out by using a unit other than electrostatic spraying.

A powder to be used for the cosmetic of the step C includes coloring pigments, extender pigments, pearl pigments and organic powder. The coloring pigments include inorganic coloring pigments, organic coloring pigments and organic coloring matters, and one or more thereof can be used.

The inorganic coloring pigments specifically include inorganic colored pigments such as red ocher, iron hydroxide, iron titanate, yellow iron oxide, black iron oxide, carbon black, Berlin blue, ultramarine blue, Berlin blue titanium oxide, black titanium oxide, titanium-titanium oxide sintered material, manganese violet, cobalt violet, chromium oxide, chromium hydroxide, cobalt oxide and cobalt titanate; and inorganic white pigments such as titanium oxide, zinc oxide, calamine, zirconium oxide, magnesium oxide, cerium oxide, aluminum oxide and composites thereof. One or more thereof can be used.

Among these, preferable is one or more selected from the group consisting of iron oxide, titanium oxide and zinc oxide; and more preferable is one or more selected from the group consisting of titanium oxide, zinc oxide, red ocher, yellow iron oxide and black iron oxide.

The organic coloring pigments and organic coloring matters include organic tar pigments such as Red No. 3, Red No. 102, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 405, Red No. 505, Orange No. 203, Orange No. 204, Orange No. 205, Yellow No. 4, Yellow No. 5, Yellow No. 401, Blue No. 1 and Blue No. 404; and organic coloring matters such as β-carotene, caramel and paprika coloring matter. Further, those covered with a polymer such as a cellulose or a polymethacrylate ester, and the like are included. Among these, it is preferable that at least Red No. 102 be contained.

The extender pigments include barium sulfate, calcium sulfate, magnesium sulfate, magnesium carbonate, calcium carbonate, talc, mica, kaolin, sericite, silicic acid, silicic acid anhydride, aluminum silicate, magnesium silicate, aluminum magnesium silicate, calcium silicate, barium silicate, strontium silicate, tungstic acid metal salts, hydroxyapatite, vermiculite, clay, bentonite, montmorillonite, hectorite, smectite, zeolite, ceramic powder, dibasic calcium phosphate, alumina, silica, aluminum hydroxide, boron nitride, synthetic mica, synthetic sericite, metallic soap, and barium sulfate-treated mica. One or more thereof can be used.

Among these, it is preferable that barium sulfate, calcium carbonate, mica, silicic acid anhydride, talc, boron nitride or synthetic mica be contained.

The pearl pigment (bright powder) includes fish scale flakes, titanium oxide-covered mica (mica titanium), bismuth oxychloride, titanium oxide-covered bismuth oxychloride, titanium oxide-covered talc, titanium oxide-covered coloring mica, titanium oxide.iron oxide-covered mica, microparticulate titanium oxide-covered mica titanium, microparticulate zinc oxide-covered mica titanium, organic pigment-treated mica titanium, low-order titanium oxide-covered mica, titanium oxide-covered synthetic mica, titanium oxide-covered tabular silica, hollow tabular titanium oxide, iron oxide-covered mica, tabular iron oxide (MIO), aluminum flakes, stainless steel flakes, titanium oxide-covered tabular alumina, glass flakes, titanium oxide-covered glass flakes, pearl shells, gold foils, gold-deposited resin films and metal-deposited resin films. One or more thereof can be used.

The organic powder includes silicone rubber powder, silicone resin-covered silicone rubber powder, polymethylsilsesquioxane powder, polyamide powder, nylon powder, polyester powder, polypropylene powder, polystyrene powder, polyurethane powder, vinyl resin powder, urea resin powder, phenol resin powder, fluororesin powder, silicone resin powder, acrylate resin powder, melamine resin powder, polycarbonate resin powder, divinylbenzene-styrene copolymer powder, silk powder, wool powder, cellulose powder, long chain-alkylphosphoric acid metal salt powder, N-mono-long chain-alkylacyl basic amino acid powder, and composite thereof. One or more thereof can be used.

Among these, it is preferable that cellulose powder, silicone rubber powder, silicone resin-covered silicone rubber powder, polymethylsilsesquioxane powder, acrylate resin powder or nylon powder be contained.

For a powder to be used for the present invention, any powder above can be used as it is, and there can also be used one or more of the powders having been subjected to a hydrophobization treatment. The hydrophobization treatment is not limited as long as it is carried out for usual cosmetic powders, and suffices if a dry treatment, a wet treatment or the like is carried out by using a surface treating agent such as a fluorocompound, a silicone-based compound, a metallic soap, an amino acid-based compound, lecithin, an alkyl silane, an oil or an organotitanate.

Specific examples of the surface-treating agent include fluorine-based compounds such as perfluoropolyethers, perfluoroalkyl phosphates, perfluoroalkylalkoxysilanes and fluorine-modified silicones; silicone-based compounds such as dimethylpolysiloxanes, methylhydrogenpolysiloxanes, cyclic silicones, one terminal or both terminals-trialkoxy group-modified organopolysiloxanes, crosslinked-type silicones, silicone resins, fluorine-modified silicone resins and acryl-modified silicones; metal soaps such as aluminum stearate, aluminum myristate, zinc stearate and magnesium stearate; amino acid-based compounds such as proline, hydroxyproline, alanine, glycine, sarcosine, glutamic acid, aspartic acid, lysine and derivatives thereof; lecithin and hydrogenated lecithin; alkylsilanes such as methyltrimethoxysilane, ethyltrimethoxysilane, hexyltrimethoxysilane, octyltrimethoxysilane and octyltriethoxysilane; oils such as polyisobutylenes, waxes and fats and oils; and organotitanates such as isopropyltitanium triisostearate.

For a powder to be used in the present invention, one or more of the powders having been subjected to a hydrophilization treatment can be used. The hydrophilization treatment is not limited as long as it is a treatment carried out for usual cosmetic powders.

Examples of the powder include vegetable-based polymers such as gum arabic, gum tragacanth, arabinogalactan, locust bean gum (carob gum), guar gum, karaya gum, carrageenan, pectin, agar, quince seed (marmelo), starch (rice, corn, potato, wheat), algae colloid, trant gum and locust bean gum; microbial polymers such as xanthan gum, dextran, succinoglucan and pullulan; animal-based polymers such as collagen, casein, albumin, and deoxyribonucleic acid (DNA) and salts thereof; starch-based polymers such as carboxymethylstarch and methylhydroxypropylstarch; cellulose-based polymers such as methylcellulose, ethylcellulose, methylhydroxypropylcellulose, carboxymethylcellulose, hydroxymethylcellulose, hydroxypropylcellulose, nitrocellulose, cellulose sodium sulfate, carboxymethylcellulose sodium, crystalline cellulose, and cellulose powder; alginic acid-based polymers such as sodium alginate and propylene glycol alginate; vinylic polymers such as polyvinyl methyl ether, polyvinylpyrrolidone and carboxyvinyl polymers; polyoxyethylene-based polymers such as polyethylene glycol and polyethylene glycol silane; polyoxyethylene polyoxypropylene copolymer-based polymers; acrylic polymers such as sodium polyacrylate, polyethyl acrylate and polyacrylic acid amide; and inorganic silicic acid-based compounds such as silica.

For powders, powders, as long as they are usually used for cosmetics, having a particle structure or the like in which their shape is spherical, plate-like, needle-like or indeterminate; they have a particle diameter of fumes, microparticles or pigments; and they are porous or nonporous; and otherwise.

The average particle diameter of the powder is, from the viewpoint of uniform close adhesion to skin hillocks, skin grooves and pores, and impartation of natural cosmetic feeling, preferably 0.001 μm or more and 200 μm or less, more preferably 0.01 μm or more and 50 μm or less, even more preferably 0.02 μm or more and 20 μm or less and further more preferably 0.05 μm or more and 10 μm or less.

In the present invention, the average particle diameter of the powder is measured by an electron microscope and a particle size distribution analyzer using a laser diffraction/scattering method. Specifically, in the case of the laser diffraction/scattering method, ethanol is used as a disperse medium and the measurement is carried out by a laser diffraction scattering type particle size distribution analyzer (for example, LMS-350, manufactured by Seishin Enterprise Co., Ltd.). Here, in the case where the powder has been subjected to the hydrophobization treatment or the hydrophilization treatment, the average particle diameter and the content of the component (c) mean an average particle diameter and a mass including those of the powder having been subjected to the hydrophobization treatment or the hydrophilization treatment.

One or more powders can be used, and the content thereof is, though depending on the form of a cosmetic, from the viewpoint of finishing, in the cosmetic, preferably 1% by mass or more, more preferably 3% by mass or more and even more preferably 5% by mass or more, and preferably 99% by mass or less, more preferably 95% by mass or less and even more preferably 90% by mass or less. The content of the powder is, in the cosmetic, preferably 1% by mass or more and 99% by mass or less, more preferably 3% by mass or more and 95% by mass or less and even more preferably 5% by mass or more and 90% by mass or less.

The mass proportion of the coloring pigments to the whole powder, [coloring pigments/whole powder], is, from the viewpoint of finishing and the viewpoint that the cosmetic containing the powder hardly kinks even after the lapse of time and is excellent in cosmetic persistency, preferably 0.2 or more, more preferably 0.3 or more and even more preferably 0.4 or more, and preferably 1.0 or less.

The kind of the cosmetic to be used for the step C is not especially limited as long as it is a powder-containing cosmetic; and the cosmetic can be applied as makeup cosmetics such as a makeup base, a foundation, a concealer, a rouge, an eye shadow, a mascara, an eyeliner, an eyebrow, an overcoat agent and a lip stick; ultraviolet-protective cosmetics such as a sun-screen milky lotion and a sun-screen cream, and the like. Among these, more preferable are the makeup base, the foundation, the concealer, the sun-screen milky lotion and the sun-screen cream.

Further the form of the cosmetic is not especially limited, and may be any of powder cosmetics, solid powder cosmetics, liquid cosmetics, oily cosmetics, emulsion cosmetics and oily solid cosmetics.

Components other than the powders contained in the cosmetic to be used in the step C include oils (including liquid oils and solid oils), emulsifiers, water-soluble polymers, fragrances, repellants, antioxidants, stabilizers, antiseptics, thickeners, pH regulators, blood circulation accelerators, various vitamins, cool sensation agents, antiperspirants, germicides, skin activators and moisturizers.

The application of the cosmetic of the step C may be carried out by a usual application unit according to the kind of a cosmetic, and the application unit includes application by spreading or pressing the foundation, for example, by using a finger or the palm of a hand, and application by spreading or pressing the foundation, for example, by using a dedicated tool. The cosmetic of the step C is a composition different from the composition X and the composition Y. Then the cosmetic of the step C may be applied by using a unit other than electrostatic spraying.

Pertaining to the above-mentioned embodiment, the present invention further discloses the following production methods, compositions and use methods of coatings.

<1> A method for producing a coating on skin, comprising:
 A) a step of electrostatically spraying a composition X comprising the following component (a) and the following component (b) directly on the skin to thereby form a coating on a skin surface:
  (a) one or more volatile substances selected from the group consisting of water, an alcohol, and a ketone, and
  (b) a polymer having a coating forming ability; and
 B) a step of applying a composition Y, other than the composition X, comprising the following component (c) and the following component (d) to the skin:
  (c) 5% by mass or more and 20% by mass or less of an adhesive polymer, and
  (d) 1% by mass or more and 40% by mass or less of a polyol,
 in this order or in reverse order.

<2> The method for producing a coating according to <1>, wherein it is preferable that the (c) adhesive polymer is one or more selected from the group consisting of a rubber-based adhesive polymer, a silicone-based adhesive polymer, an acrylic adhesive polymer and a urethane-based adhesive polymer; and it is preferable that the (c) adhesive polymer is at least one selected from the group consisting of a nonionic polymer, an anionic polymer, a cationic polymer and an amphoteric polymer.

<3> The method for producing a coating according to <1> or <2>, wherein the adhesive polymer is preferably a polymer having a maximum tensile shearing load of 1 N or more, more preferably a polymer of 3 N or more and even more preferably a polymer of 5 N or more.

<4> The method for producing a coating according to any one of <1> to <3>, wherein the content of the (c) adhesive polymer in the composition Y is preferably 6% by mass or more; and the content is preferably 15% by mass or less, more preferably 12% by mass or less and even more preferably 10% by mass or less, and preferably 5% by mass or more and 15% by mass or less, more preferably 5% by mass or more and 12% by mass or less and even more preferably 5% by mass or more and 10% by mass or less.

<5> The method for producing a coating according to any one of <1> to <4>, wherein as the polyol to be used for the composition Y, preferable are alkylene glycols such as ethylene glycol, propylene glycol, 1,3-propanediol and 1,3-butanediol; polyalkylene glycols such as diethylene glycol, dipropylene glycol, and polyethylene glycols and polypropylene glycols having a weight-average molecular weight of 1,000 or less; and glycerols such as glycerol, diglycerol and triglycerol; preferable are ethylene glycol, propylene glycol, 1,3-butanediol, dipropylene glycol, polyethylene glycol having a weight-average molecular weight of 1,000 or less, glycerol and diglycerol; and more preferable are propylene glycol, 1,3-butanediol and glycerol; and even more preferable is glycerols.

<6> The method for producing a coating according to any one of <1> to <5>, wherein the contain of the component (d) in the composition Y is preferably 1% by mass or more and 40% by mass or less, more preferably 1% by mass or more and 30% by mass or less, even more preferably 3% by mass or more and 25% by mass or less, further more preferably 5% by mass or more and 20% by mass or less and further more preferably 10% by mass or more and 20% by mass or less.

<7> The method for producing a coating according to any one of <1> to <6>, wherein the mass proportion of the component (d) to the component (c) in the composition Y, ((d)/(c)), is preferably 0.1 or more and 8 or less, more preferably 0.2 or more and 7 or less and even more preferably 0.3 or more and 6 or less.

<8> The method for producing a coating according to any one of <1> to <7>, wherein it is preferable that the composition Y further comprises a component (e), an oil, and comprises one or more selected from the group consisting of a liquid oil (oil liquid at 20° C.) and a solid oil (oil solid at 20° C.)

<9> The method for producing a coating according to <8>, wherein the liquid oil (oil liquid at 20° C.) is one or more selected from the group consisting of a hydrocarbon oil, an ester oil, a plant oil, a higher alcohol, a silicone oil and a fatty acid.

<10> The method for producing a coating according to <8> or <9>, wherein the oil solid at 20° C. is one or more selected from the group consisting of a hydrocarbon wax, an ester wax, a paraoxybenzoate ester, a fatty acid ester, a higher alcohol, an ester of a straight-chain fatty acid having 14 or more carbon atoms, a triglyceride containing three straight-chain fatty acids having 12 or more carbon atoms as constituents and a silicone wax.

<11> The method for producing a coating according to any one of <8> to <10>, wherein the content of the component (e) in the composition Y is preferably 1% by mass or more and 20% by mass or less, more preferably 2% by mass or more and 18% by mass or less and even more preferably 3% by mass or more and 16% by mass or less.

<12> The method for producing a coating according to any one of <8> to <11>, wherein the mass proportion of the component (e) to the component (c), ((e)/(c)), in the composition Y is preferably 0.06 or more and 4 or less, more preferably 0.07 or more and 3.5 or less and even more preferably 0.08 or more and 3 or less.

<13> The method for producing a coating according to any one of <1> to <12>, wherein the step (B) applies the composition to the skin by using a unit other than electrostatic spraying.

<14> The method for producing a coating according to any one of <1> to <13>, wherein the method is preferably a method of applying a cosmetic comprising a powder to the skin before, between or after the step A and the step B; and the steps can be carried out in the order of the step A, the step B and the step C, or in the order of the step B, the step A and the step C, or the step B, the step A, the step C, the step A and the step B.

<15> The method for producing a coating according to any one of <1> to <14>, wherein the coating formed by electrostatic spraying in the step A) is a porous coating.

<16> The method for producing a coating according to any one of <1> to <15>, wherein the step A) is a step of electrostatically spraying the composition X on the skin by using an electrostatic spray apparatus to thereby form a coating made of a deposit of a fiber, the electrostatic spray apparatus comprising a container for accommodating the composition X, a nozzle for discharging the composition X, a feed device for feeding the composition X accommodated in the container to the nozzle, and a power source for applying a voltage to the nozzle.

<17> A composition Y for applying to a skin, wherein the composition Y is a composition used for producing a coating on skin by applying the composition to the skin by using a unit other than electrostatic spraying, before or after a coating is formed on a skin surface by electrostatically spraying a composition directly on the skin, and comprises the following component (c) and the following component (d):

(c) 5% by mass or more and 20% by mass or less of an adhesive polymer, and (d) 1% by mass or more and 40% by mass or less of a polyol.

<18> A method for applying a composition Y to skin, the method being a method used for producing a coating on the skin by applying the composition Y to the skin by using a unit other than electrostatic spraying, before or after a coating is formed on a skin surface by electrostatically spraying a composition directly on the skin, wherein the composition Y comprises the following component (c) and the following component (d):

(c) 5% by mass or more and 20% by mass or less of an adhesive polymer, and (d) 1% by mass or more and 40% by mass or less of a polyol.

EXAMPLES

Hereinafter, the present invention will be described in more detail by way of Examples. However, the scope of the present invention is not limited to these Examples. Unless otherwise specified, "%" means "mass %".

Synthesis Example 1 (Production of a poly(N-propionylethyleneimine)-Modified Silicone)

19.0 g (0.12 mol) of diethyl sulfate and 81.0 g (0.82 mol) of 2-ethyl-2-oxazoline were dissolved in 203.0 g of dehydrated ethyl acetate, and heated and refluxed in a nitrogen atmosphere for 8 hours to thereby synthesize a terminal-reactive poly(N-propionylethyleneimine). The number-average molecular weight was measured by GPC, and was 1,100. Thereto, a 33% ethyl acetate solution of 300 g of a side chain-primary aminopropyl-modified polydimethylsiloxane (weight-average molecular weight: 32,000, amine equivalent: 2,000) was collectively added, and heated and refluxed for 10 hours. The reaction mixture was concentrated under reduced pressure to thereby obtain an N-propionylethyleneimine-dimethylsilozane copolymer as a light yellow rubbery solid (390 g, yield:)97°. The content rate of an organopolysiloxane segment in the final product was 75% by mass and the weight-average molecular weight was 40,000. As a result of neutralization titration with hydrochloric acid using methanol as a solvent, it was found that about 20 mol % of the amino group remained. This adhesive polymer had a maximum tensile shearing load of 8.6 N as measured according to JIS K6850.

Further the measurement results of the maximum tensile shearing load of commercially available adhesive polymers are shown in Table 1.

Thereafter, the sensory evaluation was carried out on the coating formed on the artificial leather, according to the following criteria.

[Evaluations]
(1) Scratch resistance

The scratch resistance of the coating was evaluated by a scratch test at a high load. The artificial leather was fixed on

TABLE 1

| Raw Material Name (Maker Name) | Polymer Name | Maximum Tensile Shearing Load (N) |
|---|---|---|
| Kollidon 90F | polyvinylpyrrolidone | 54.6 |
| Synthesis Example 1 | poly(N-propionylethyleneimine)-modified silicone | 8.6 |
| Baycusan C2000 (COVESTRO AG) | polyurethane-64 | 48.2 |
| PEG 20000 | polyethylene glycol (molecular weight: 20,000) | 3.4 |
| Amphomer 28-4910 (Akzo Nobel N.V.) | (octylacrylamide/acrylate/butylaminoethyl methacrylate) copolymer | 20.5 |
| Amphomer LV-71 (Akzo Nobel N.V.) | (octylacrylamide/hydroxypropyl acrylate/butylaminoethyl methacrylate) copolymer | 32.3 |
| Amphomer HC (Akzo Nobel N.V.) | (alkyl acrylate-octylacrylamide) copolymer | 9.7 |
| Resyn 28-2930 (Akzo Nobel N.V.) | (VA/crotonic acid/vinyl neodecanoate) copolymer | 65.7 |
| Gantrez ES425 (Ashland Inc.) | (vinyl methyl ether/butyl maleate) copolymer | 25.0 |
| Omnirez 2000 (Ashland Inc.) | (vinyl methyl ether/ethyl maleate) copolymer | 34.7 |
| Yodosol GH34F (Akzo Nobel N.V.) | alkyl acrylate copolymer ammonium | 40.5 |
| Yodosol GH800F (Akzo Nobel N.V.) | alkyl acrylate copolymer ammonium | 27.3 |
| Diaformer Z651 (Mitsubishi Chemical Corp.) | (acrylate/lauryl acrylate/stearyl acrylate/ethyl methacrylate amine oxide) copolymer | 80.7 |
| Yukaformer 301 (Mitsubishi Chemical Corp.) | (methacryloyloxyethylcarboxybetaine/alkyl methacrylate) copolymer | 34.0 |
| Yukaformer 104D (Mitsubishi Chemical Corp.) | (methacryloyloxyethylcarboxybetaine/alkyl methacrylate) copolymer | 64.0 |
| Yukaformer 202 (Mitsubishi Chemical Corp.) | (methacryloyloxyethylcarboxybetaine/alkyl methacrylate) copolymer | 79.6 |
| Yukaformer SM (Mitsubishi Chemical Corp.) | (methacryloyloxyethylcarboxybetaine/alkyl methacrylate) copolymer | 57.4 |
| Yukaformer R205S (Mitsubishi Chemical Corp.) | (methacryloyloxyethylcarboxybetaine/alkyl methacrylate) copolymer | 41.1 |
| Baycusan C1004 (COVESTRO AG) | Polyurethane-35 | 66.9 |
| Daitosol 5000SJ (Daito Kasei Kogyo Co., Ltd.) | acrylates/ethylhexyl acrylate copolymer | 29.4 |

[Test 1]
(1) Preparation of a spraying composition (composition X)

Spraying compositions used were compositions in Table 2.

(2) Preparation of compositions Y

Compositions Y used were liquid agents (compositions Y) in Table 3 to Table 10.

(3) Evaluation step (i) A commercially available skin care agent was applied to an artificial leather (manufactured by Idemitsu Technofine Co., Ltd., Protein Leather PBZ13001BK) of 0.7 mm in thickness.

(ii) The composition Y was applied (step B). 200 mg of the composition Y was taken on a sponge and then applied to the range of 5 cm×5 cm of the artificial leather. The amount applied on the artificial leather was 40 mg.

(iii) The electrostatic spraying (step A) was carried out.

By using an electrostatic spray apparatus 10 having s constitution shown in FIG. 1 and having an appearance illustrated in FIG. 2, an electrostatic spray method was carried out toward the region on the artificial leather where the composition had been applied, for 60 s. The condition of the electrostatic spray method was as follows.
Applied voltage: 10 kV
Distance between a nozzle and the skin: 100 mm
Amount of a spraying composition discharged: 5 mL/h
Environment: 25° C., 30% RH By the electrostatic spraying, a porous coating composed of a deposit of fibers was formed on the artificial leather surface. The coating was applied in a square shape of 7 cm×7 cm.

(iv) The coating was lightly pressed by a finger, a sponge or the like to make the coating to conform to the composition Y, and thereafter, dried at room temperature for 2 or more hours.

an electronic balance with a double-sided tape. The corner of a screw-capped bottle (manufactured by Maruemu Corp., No. 4) having a cloth (cotton knit cloth) affixed with a double-sided tape thereon was pressed at a force of 500 gf on the surface of the formed coating. With the load of 500 gf being applied, the scratch test was carried out in a horizontal movement of 7 cm from an outside of the range where the composition Y had been applied to the opposite side thereof. The durability of the coating was evaluated according to the state of being peeled off the artificial leather, in the following criteria.

Evaluation criteria:
A: Even after 50 times of scratching test, no portion of complete peeling-off was observed in the range where the composition Y had been applied;
B: In 31 to 50 times of the scratching test, a portion of complete peeling-off was produced in the range where the composition Y had been applied;
C: In 11 to 30 times of the scratching test, a portion of complete peeling-off was produced in the range where the composition Y had been applied; and
D: In 1 to 10 times of the scratching test, a portion of complete peeling-off was produced in the range where the composition Y had been applied.

(2) Extensibility

Both ends of sides of 10 cm of the formed coating (artificial leather) were pulled to 12 cm by hand, and there was evaluated whether or not wrinkle, lift or crack was generated.

Evaluation criteria:
A: In one time of tensile test, no change occurred in the appearance of the coating in the range where the composition Y had been applied;
B: In one time of the tensile test, wrinkle, lift or crack was generated in 50% or less of the area of the coating in the range where the composition Y had been applied;

C: In one time of the tensile test, wrinkle, lift or crack was generated in 50% or more of the area of the coating in the range where the composition Y had been applied; and D: In one time of the tensile test, the coating in the range where the composition Y had been applied was completely peeled off.

TABLE 2

Spraying Composition

| Component | w/w (%) |
|---|---|
| Ethanol | 79.60% |
| Water | 0.40% |
| Polyvinyl Butyral *1 | 12.00% |
| Butylene Glycol | 7.50% |
| Distearyldimonium Chloride | 0.50% |

*1: S-Lec B BM-1 (Sekisui Chemical Co., Ltd.)

TABLE 3

| Component | Composition Y | | | | |
|---|---|---|---|---|---|
| | 1 | 2 | 3 | 4 | 5 |
| Deionized water | 75.495% | 74.338% | 72.024% | 69.709% | 67.395% |
| Glycerin | 10.000% | 10.000% | 10.000% | 10.000% | 10.000% |
| Methyl Paraben | 0.200% | 0.200% | 0.200% | 0.200% | 0.200% |
| Ethyl Paraben | 0.100% | 0.100% | 0.100% | 0.100% | 0.100% |
| Aminomethylpropanol | 0.000% | 0.157% | 0.471% | 0.786% | 1.100% |
| Octylacrylamide/Butylaminoethyl Methacrylate Copolymer (Amphomer 28-4910) | 0.000% | 1.000% | 3.000% | 5.000% | 7.000% |
| Magnesium Aluminum Silicate | 0.100% | 0.100% | 0.100% | 0.100% | 0.100% |
| Mineral Oil | 5.000% | 5.000% | 5.000% | 5.000% | 5.000% |
| Ceteareth-20 | 0.250% | 0.250% | 0.250% | 0.250% | 0.250% |
| Cetearyl Alcohol | 1.000% | 1.000% | 1.000% | 1.000% | 1.000% |
| Mineral Oil, Ethylene/Propylene/Styrene Copolymer, Butylene/Ethylene/Styrene Copolymer (versagel M200) | 7.500% | 7.500% | 7.500% | 7.500% | 7.500% |
| Acrylates/C10-30 Alkyl Acrylate Crosspolymer (Pemulen TR-1) | 0.300% | 0.300% | 0.300% | 0.300% | 0.300% |
| Sodium Hydroxide (48%) | 0.055% | 0.055% | 0.055% | 0.055% | 0.055% |
| Scratch Resistance | D | D | D | A | A |
| Extensibility | C | B | A | A | A |

From Table 3, it is clear that the (c) adhesive polymer has to be contained in 5% by mass or more in the composition Y.

TABLE 4

| Component | Composition Y |
|---|---|
| Ethanol | 91.900% |
| Aminomethylpropanol | 1.10% |
| Octylacrylamide/Butylaminoethyl Methacrylate Copolymer (Amphomer 28-4910) | 7.00% |
| Scratch Resistance | A |
| Extensibility | C |

TABLE 5

| Component | Composition Y | |
|---|---|---|
| | 7 | 8 |
| Deionized water | 77.395% | 67.395% |
| Glycerin | 0.00% | 10.00% |
| Methyl Paraben | 0.20% | 0.20% |
| Ethyl Paraben | 0.10% | 0.10% |
| Aminomethylpropanol | 1.10% | 1.10% |
| Octylacrylamide/Butylaminoethyl Methacrylate Copolymer (Amphomer 28-4910) | 7.00% | 7.00% |
| Magnesium Aluminum Silicate | 0.10% | 0.10% |
| Mineral Oil | 5.00% | 5.00% |
| Ceteareth-20 | 0.25% | 0.25% |
| Cetearyl Alcohol | 1.00% | 1.00% |
| Mineral Oil, Ethylene/Propylene/Styrene Copolymer, Butylene/Ethylene/Styrene Copolymer (versagel M200) | 7.50% | 7.50% |
| Acrylates/C10-30 Alkyl Acrylate Crosspolymer (Pemulen TR-1) | 0.30% | 0.30% |
| Sodium Hydroxide (48%) | 0.055% | 0.055% |
| Scratch Resistance | D | A |
| Extensibility | C | A |

From Table 4 and Table 5, it is clear that a polyol has to be contained in the composition Y.

TABLE 6

| Component | Composition Y 9 | Composition Y 10 | Composition Y 11 |
|---|---|---|---|
| Deionized water | 74.895% | 74.895% | 74.895% |
| Glycerin | 10.00% | 10.00% | 10.00% |
| Methyl Paraben | 0.20% | 0.20% | 0.20% |
| Ethyl Paraben | 0.10% | 0.10% | 0.10% |
| Aminomethylpropanol | 1.10% | 1.10% | 1.10% |
| Octylacrylamide/Butylaminoethyl Methacrylate Copolymer (Amphomer 28-4910) | 7.00% | 7.00% | 7.00% |
| Magnesium Aluminum Silicate | 0.10% | 0.10% | 0.10% |
| Mineral Oil | 5.00% | 0.00% | 0.00% |
| Olive Oil + Tocopherol(Cropure OL-LQ- (JP)) | 0.00% | 5.00% | 0.00% |
| Isononyl isononanoate(Salacos 913) | 0.00% | 0.00% | 5.00% |
| Ceteareth-20 | 0.25% | 0.25% | 0.25% |
| Cetearyl Alcohol | 1.00% | 1.00% | 1.00% |
| Acrylates/C10-30 Alkyl Acrylate Crosspolymer (Pemulen TR-1) | 0.30% | 0.30% | 0.30% |
| Sodium Hydroxide (48%) | 0.055% | 0.055% | 0.055% |
| Scratch Resistance | C | A | A |
| Extensibility | A | A | A |

TABLE 7

| Component | Composition Y 12 | Composition Y 13 | Composition Y 14 |
|---|---|---|---|
| Deionized water | 79.895% | 76.895% | 74.895% |
| Glycerin | 10.00% | 10.00% | 10.00% |
| Methyl Paraben | 0.20% | 0.20% | 0.20% |
| Ethyl Paraben | 0.10% | 0.10% | 0.10% |
| Aminomethylpropanol | 1.10% | 1.10% | 1.10% |
| Octylacrylamide/Butylaminoethyl Methacrylate Copolymer (Amphomer 28-4910) | 7.00% | 7.00% | 7.00% |
| Magnesium Aluminum Silicate | 0.10% | 0.10% | 0.10% |
| Mineral Oil | 0.00% | 3.00% | 5.00% |
| Ceteareth-20 | 0.25% | 0.25% | 0.25% |
| Cetearyl Alcohol | 1.00% | 1.00% | 1.00% |
| Acrylates/C10-30 Alkyl Acrylate Crosspolymer (Pemulen TR-1) | 0.30% | 0.30% | 0.30% |
| Sodium Hydroxide (48%) | 0.055% | 0.055% | 0.055% |
| Scratch Resistance | B | A | C |
| Extensibility | A | A | A |

From Table 6 and Table 7, it is clear that addition of an oil component in addition to a polyol in the composition Y improves especially the extensibility.

TABLE 8

| Component | Composition Y 15 |
|---|---|
| Deionized water | 72.9% |
| Glycerin | 10.0% |
| Polyurethane dispersion (41% Polyurethane-35: Baycusan C1004 (Covestro Deutschland AG)) | 17.1% |
| Scratch resistance | C |
| Extensibility | A |

TABLE 9

| Component | Composition Y 16 |
|---|---|
| Deionized water | 50% |
| Glycerin | 10% |
| Acrylates/Ethylhexyl Acrylate Copolymer (Daitosol 5000sj catc.50: Daito Kasei) | 40% |
| Scratch resistance | A |
| Extensibility | A |

TABLE 10

| Component | Composition Y 17 | Composition Y 18 | Composition Y 19 | Composition Y 20 |
|---|---|---|---|---|
| Deionized water | 81.9% | 71.9% | 81.9% | 81.9% |
| Glycerin | 10.0% | 20.0% | — | — |
| Polyethylene glycol (PEG400) | — | — | 10.0% | — |
| Diglycerin | — | — | — | 10.0% |
| (Octylacrylamide/Hydroxypropyl Acrylate/Butylaminoethyl methacrylate)copolymer (Amphomer 28-4910) | 7.0% | 7.0% | 7.0% | 7.0% |
| Aminomethyl propanol | 1.1% | 1.1% | 1.1% | 1.1% |
| Scratch resistance | C | C | B | C |
| Extensibility | B | A | A | A |

[Test 2]
(1) Preparation of a spray composition (composition X)
   The composition of Table 11 was used as a spray composition.
(2) Preparation of composition Y The composition Y (9) in Table 6 was used.

(3) Scratch resistance and extensibility were evaluated in the same manner as described in the above Test 1. The result is shown in Table 11.

TABLE 11

| Component | Spray composition (composition X) 21 |
|---|---|
| Ethanol | 86.1% |
| Water | 0.4% |
| Polyvinyl Butyral*2 | 6.0% |
| 1,3-Butylene glycol | 7.5% |
| Scratch resistance | B |
| Extensibility | A |

*2 Mowital B 75H (Kuraray Co., Ltd)

REFERENCE SIGNS LIST

10 ELECTROSTATIC SPRAY APPARATUS
11 LOW-VOLTAGE POWER SOURCE
12 HIGH-VOLTAGE POWER SOURCE
13 AUXILIARY ELECTRIC CIRCUIT
14 PUMP MECHANISM
15 CONTAINER
16 NOZZLE
17 PIPE
18 FLEXIBLE PIPE
19 CURRENT LIMITING RESISTANCE
20 HOUSING

The invention claimed is:

1. A method for producing a coating on skin, comprising:

A) electrostatically spraying a composition X comprising the following components (a) and (b) directly on the skin to thereby form a coating on a skin surface:

(a) one or more volatile substances selected from the group consisting of water, an alcohol, and a ketone, and (b) a polymer having a coating formability; and B) applying a composition Y, other than the composition X, comprising the following components (c) and (d) to the skin:

(c) 5% by mass or more and 20% by mass or less of an adhesive polymer, and (d) 1% by mass or more and 40% by mass or less of a polyol, in this order or in reverse order, wherein said adhesive polymer has a maximum tensile shear load of 1 N or more, and wherein a mass proportion of the component (d) to the component (c), ((d)/(c)), in the composition Y is 0.1 or more and 6 or less.

2. The method for producing a coating according to claim 1, wherein the composition Y further comprises (e) an oil.

3. The method for producing a coating according to claim 2, wherein a content of the component (e) in the composition Y is 1% by mass or more and 20% by mass or less.

4. The method for producing a coating according to claim 2, wherein a mass proportion of the component (e) to the component (c), ((e)/(c)), is 0.06 or more and 4 or less.

5. The method for producing a coating according to claim 2, wherein the composition Y is an oil-in-water emulsion composition.

6. The method for producing a coating according to claim 1, wherein said B) applying the composition Y to the skin is conducted with a device other than an electrostatic spraying device.

7. The method for producing a coating according to claim 1, wherein the coating formed by the electrostatic spraying in the step A) is a porous coating.

8. The method for producing a coating according to claim 1, wherein said A) electrostatically spraying the composition X on skin is conducted with an electrostatic spray device to thereby form a coating made of a fiber deposit, the electrostatic spray device comprising a container for accommodating the composition X, a nozzle for discharging the composition X, a feed device for feeding the composition X accommodated in the container to the nozzle, and a power source for applying a voltage to the nozzle.

9. A composition Y for being applied to skin, wherein the composition Y is a composition used for producing a coating on skin by applying the composition to the skin by using a device other than an electrostatic spray device, before or after a coating is formed on a skin surface by electrostatically spraying a composition directly on the skin, and comprises the following component (c) and the following component (d):

(c) 5% by mass or more and 20% by mass or less of an adhesive polymer, and (d) 1% by mass or more and 40% by mass or less of a polyol, wherein said adhesive polymer has a maximum tensile shear load of 1 N or more, and wherein a mass proportion of the component (d) to the component (c), ((d)/(c)), in the composition Y is 0.1 or more and 6 or less.

10. The composition Y according to claim 9, wherein the composition used for the electrostatic spraying is a composition X comprising the following components (a) and (b):

(a) one or more volatile substances selected from the group consisting of water, an alcohol, and a ketone, and (b) a polymer having a coating formability.

11. A method for applying a composition Y to skin, the method being a method used for producing a coating on the skin by applying the composition Y to the skin by using a unit other than electrostatic spraying, before or after a coating is formed on a skin surface by electrostatically spraying a composition directly on the skin, wherein the composition Y comprises the following components (c) and (d):

(c) 5% by mass or more and 20% by mass or less of an adhesive polymer, and (d) 1% by mass or more and 40% by mass or less of a polyol, wherein said adhesive polymer has a maximum tensile shear load of 1 N or more, and wherein a mass proportion of the component (d) to the component (c), ((d)/(c)), in the composition Y is 0.1 or more and 6 or less.

12. The method according to claim 11, wherein the composition used for the electrostatic spraying is a composition X comprising the following components (a) and (b):

(a) one or more volatile substances selected from the group consisting of water, an alcohol, and a ketone, and (b) a polymer having a coating formability.

13. The method for producing a coating according to claim 1, wherein said adhesive polymer has a maximum tensile shearing load as measured by JIS K6850 of 3 N or more and 200 N or less.

14. The method for producing a coating according to claim 1, wherein said adhesive polymer has a maximum tensile shearing load as measured by JIS K6850 of 5 N or more and 150 N or less.

15. The composition according to claim 9, wherein said adhesive polymer has a maximum tensile shearing load as measured by JIS K6850 of 3 N or more and 200 N or less.

16. The composition according to claim 9, wherein said adhesive polymer has a maximum tensile shearing load as measured by JIS K6850 of 5 N or more and 150 N or less.

17. The method according to claim 11, wherein said adhesive polymer has a maximum tensile shearing load as measured by JIS K6850 of 3 N or more and 200 N or less.

18. The method according to claim 11, wherein said adhesive polymer has a maximum tensile shearing load as measured by JIS K6850 of 5 N or more and 150 N or less.

19. The method according to claim 1, wherein said adhesive polymer is one or more members selected from the group consisting of a rubber-based adhesive polymer, a poly(N-acylalkyleneimine)-modified organopolysiloxane, an acrylic adhesive polymer, and a urethane-based adhesive polymer.

20. The method according to claim 1, wherein said composition Y further comprises (e) one or more oils in a liquid state at 20° C. selected from the group consisting of a hydrocarbon oil, an ester oil, a higher alcohol, a silicone oil, and a fatty acid.

* * * * *